United States Patent
Gliner

(10) Patent No.: US 8,126,568 B2
(45) Date of Patent: Feb. 28, 2012

(54) ELECTRODE GEOMETRIES FOR EFFICIENT NEURAL STIMULATION

(75) Inventor: Bradford Evan Gliner, Sammamish, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1362 days.

(21) Appl. No.: 11/697,698

(22) Filed: Apr. 6, 2007

(65) Prior Publication Data

US 2007/0179584 A1 Aug. 2, 2007

Related U.S. Application Data

(62) Division of application No. 10/112,301, filed on Mar. 28, 2002, now Pat. No. 7,221,981.

(51) Int. Cl.
*A61N 1/05* (2006.01)

(52) U.S. Cl. .................................. 607/116; 607/117

(58) Field of Classification Search .................. 607/116, 607/45, 117, 129
See application file for complete search history.

(56) References Cited

U.S. PATENT DOCUMENTS

| | | |
|---|---|---|
| 2,716,226 A | 8/1955 | Jonas |
| 2,721,316 A | 10/1955 | Shaw |
| 3,628,193 A | 12/1971 | Collins |
| 3,650,276 A | 3/1972 | Burghele et al. |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Picard et al. |
| 4,308,868 A | 1/1982 | Jhabvala |
| 4,328,813 A | 5/1982 | Ray |
| 4,340,038 A | 7/1982 | McKean |
| 4,431,000 A | 2/1984 | Butler et al. |
| 4,474,186 A | 10/1984 | Ledley et al. |
| 4,542,752 A | 9/1985 | Dehaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |

(Continued)

FOREIGN PATENT DOCUMENTS

DE 19750043 5/1999

(Continued)

OTHER PUBLICATIONS

U.S. Appl. No. 10/583,630, filed Jun. 20, 2006, Lozano.

(Continued)

*Primary Examiner* — Kennedy Schaetzle

(74) *Attorney, Agent, or Firm* — Christopher S. L. Crawford; Craig Hoersten; Pete Lando

(57) ABSTRACT

Electrodes designed in accordance with the present invention may selectively employ arc shaped contacts; variations in contact number, positioning, spacing, and/or distribution; variations in contact area, size, or periphery; and/or on-electrode conductive links or interconnections between particular contacts to provide enhanced efficiency neural stimulation, and/or increased electrode reliability.

7 Claims, 14 Drawing Sheets

U.S. PATENT DOCUMENTS

| | | | |
|---|---|---|---|
| 5,054,906 A | 10/1991 | Lyons | |
| 5,063,932 A | 11/1991 | Dahl et al. | |
| 5,092,835 A | 3/1992 | Schurig et al. | |
| 5,121,754 A | 6/1992 | Mullett | |
| 5,143,089 A | 9/1992 | Alt | |
| 5,169,384 A | 12/1992 | Bosniak et al. | |
| 5,184,620 A | 2/1993 | Cudahy et al. | |
| 5,193,540 A | 3/1993 | Schulman et al. | |
| 5,215,086 A | 6/1993 | Terry, Jr. et al. | |
| 5,224,491 A | 7/1993 | Mehra | |
| 5,255,678 A | 10/1993 | Deslauriers et al. | |
| 5,263,967 A | 11/1993 | Lyons, III et al. | |
| 5,269,319 A * | 12/1993 | Schulte et al. | 607/123 |
| 5,271,417 A | 12/1993 | Swanson et al. | |
| 5,282,468 A | 2/1994 | Klepinski | |
| 5,299,569 A | 4/1994 | Wernicke et al. | |
| 5,303,705 A | 4/1994 | Nenov | |
| 5,304,206 A | 4/1994 | Baker, Jr. et al. | |
| 5,314,458 A | 5/1994 | Najafi et al. | |
| 5,358,513 A | 10/1994 | Powell, III et al. | |
| 5,370,672 A | 12/1994 | Fowler et al. | |
| 5,405,375 A | 4/1995 | Ayers et al. | |
| 5,406,957 A | 4/1995 | Tansey | |
| 5,411,540 A | 5/1995 | Edell et al. | |
| 5,417,719 A | 5/1995 | Hull et al. | |
| 5,423,864 A | 6/1995 | Ljungstroem | |
| 5,464,446 A | 11/1995 | Dreessen et al. | |
| 5,520,190 A | 5/1996 | Benedict et al. | |
| 5,522,864 A | 6/1996 | Wallace et al. | |
| 5,537,512 A | 7/1996 | Hsia et al. | |
| 5,540,734 A | 7/1996 | Zabara | |
| 5,540,736 A | 7/1996 | Haimovish et al. | |
| 5,549,655 A | 8/1996 | Erickson | |
| 5,562,708 A | 10/1996 | Combs et al. | |
| 5,575,813 A | 11/1996 | Edell et al. | |
| 5,591,216 A | 1/1997 | Testerman et al. | |
| 5,593,432 A | 1/1997 | Crowther et al. | |
| 5,601,611 A | 2/1997 | Fayram et al. | |
| 5,611,350 A | 3/1997 | John | |
| 5,618,531 A | 4/1997 | Cherksey | |
| 5,628,317 A | 5/1997 | Starkebaum et al. | |
| 5,643,338 A * | 7/1997 | Bornzin et al. | 607/123 |
| 5,674,251 A | 10/1997 | Combs et al. | |
| 5,676,655 A | 10/1997 | Howard, III et al. | |
| 5,683,422 A | 11/1997 | Rise | |
| 5,702,429 A | 12/1997 | King | |
| 5,707,334 A | 1/1998 | Young | |
| 5,711,316 A | 1/1998 | Elsberry et al. | |
| 5,713,922 A | 2/1998 | King | |
| 5,713,923 A | 2/1998 | Ward et al. | |
| 5,716,377 A | 2/1998 | Rise et al. | |
| 5,722,401 A | 3/1998 | Pietroski | |
| 5,735,814 A | 4/1998 | Elsberry et al. | |
| 5,750,376 A | 5/1998 | Weiss et al. | |
| 5,752,979 A | 5/1998 | Benabid | |
| 5,769,778 A | 6/1998 | Abrams et al. | |
| 5,772,591 A | 6/1998 | Cram | |
| 5,782,798 A | 7/1998 | Rise | |
| 5,782,873 A | 7/1998 | Collins | |
| 5,792,186 A | 8/1998 | Rise | |
| 5,797,970 A | 8/1998 | Pouvreau | |
| 5,814,014 A | 9/1998 | Elsberry et al. | |
| 5,814,092 A | 9/1998 | King | |
| 5,824,021 A | 10/1998 | Rise | |
| 5,824,030 A | 10/1998 | Yang et al. | |
| 5,832,932 A | 11/1998 | Elsberry et al. | |
| 5,833,709 A | 11/1998 | Rise et al. | |
| 5,843,148 A | 12/1998 | Gijsbers et al. | |
| 5,843,150 A | 12/1998 | Dreessen et al. | |
| 5,865,842 A | 2/1999 | Knuth et al. | |
| 5,871,517 A | 2/1999 | Abrams et al. | |
| 5,885,976 A | 3/1999 | Sandyk | |
| 5,886,769 A | 3/1999 | Zolten | |
| 5,893,883 A | 4/1999 | Torgerson et al. | |
| 5,904,916 A | 5/1999 | Hirsch | |
| 5,913,882 A | 6/1999 | King | |
| 5,916,171 A | 6/1999 | Mayevsky | |
| 5,925,070 A | 7/1999 | King et al. | |
| 5,938,688 A | 8/1999 | Schiff | |
| 5,938,689 A | 8/1999 | Fischell et al. | |
| 5,941,906 A | 8/1999 | Barreras, Sr. et al. | |
| 5,964,794 A | 10/1999 | Bolz et al. | |
| 5,975,085 A | 11/1999 | Rise | |
| 5,978,702 A | 11/1999 | Ward et al. | |
| 5,983,140 A | 11/1999 | Smith et al. | |
| 6,006,124 A | 12/1999 | Fischell et al. | |
| 6,011,996 A | 1/2000 | Gielen et al. | |
| 6,016,449 A | 1/2000 | Fischell et al. | |
| 6,018,682 A | 1/2000 | Rise | |
| 6,021,352 A | 2/2000 | Christopherson et al. | |
| 6,026,326 A | 2/2000 | Bardy | |
| 6,035,236 A | 3/2000 | Jarding et al. | |
| 6,040,180 A | 3/2000 | Johe | |
| 6,042,579 A | 3/2000 | Elsberry et al. | |
| 6,052,624 A | 4/2000 | Mann | |
| 6,055,456 A | 4/2000 | Gerber | |
| 6,057,846 A | 5/2000 | Sever, Jr. | |
| 6,057,847 A | 5/2000 | Jenkins | |
| 6,058,331 A | 5/2000 | King | |
| 6,060,048 A | 5/2000 | Cherksey | |
| 6,061,593 A | 5/2000 | Fischell et al. | |
| 6,066,163 A | 5/2000 | John | |
| 6,095,148 A | 8/2000 | Shastri et al. | |
| 6,104,956 A | 8/2000 | Naritoku et al. | |
| 6,104,960 A | 8/2000 | Duysens et al. | |
| 6,122,548 A | 9/2000 | Starkebaum et al. | |
| 6,126,657 A | 10/2000 | Edwards et al. | |
| 6,128,537 A | 10/2000 | Rise | |
| 6,128,538 A | 10/2000 | Fischell et al. | |
| 6,134,474 A | 10/2000 | Fischell et al. | |
| 6,152,143 A | 11/2000 | Edwards | |
| 6,161,044 A | 12/2000 | Silverstone | |
| 6,161,045 A | 12/2000 | Fischell et al. | |
| 6,176,242 B1 | 1/2001 | Rise | |
| 6,190,893 B1 | 2/2001 | Shastri et al. | |
| 6,198,958 B1 | 3/2001 | Ives et al. | |
| 6,205,360 B1 | 3/2001 | Carter et al. | |
| 6,210,417 B1 | 4/2001 | Baudino et al. | |
| 6,221,908 B1 | 4/2001 | Kilgard et al. | |
| 6,230,049 B1 | 5/2001 | Fischell et al. | |
| 6,236,892 B1 | 5/2001 | Feler | |
| 6,246,912 B1 | 6/2001 | Sluijter et al. | |
| 6,280,462 B1 | 8/2001 | Hauser et al. | |
| 6,301,493 B1 | 10/2001 | Marro et al. | |
| 6,319,241 B1 | 11/2001 | King et al. | |
| 6,339,725 B1 | 1/2002 | Naritoku et al. | |
| 6,353,754 B1 | 3/2002 | Fischell et al. | |
| 6,354,299 B1 | 3/2002 | Fischell et al. | |
| 6,356,792 B1 | 3/2002 | Errico et al. | |
| 6,360,122 B1 | 3/2002 | Fischell et al. | |
| 6,366,813 B1 | 4/2002 | DiLorenzo | |
| 6,375,666 B1 | 4/2002 | Mische | |
| 6,405,079 B1 | 6/2002 | Ansarinia | |
| 6,418,344 B1 | 7/2002 | Rezai | |
| 6,427,086 B1 | 7/2002 | Fischell et al. | |
| 6,456,886 B1 | 9/2002 | Howard, III et al. | |
| 6,459,936 B2 | 10/2002 | Fischell et al. | |
| 6,463,328 B1 | 10/2002 | John | |
| 6,464,356 B1 | 10/2002 | Sabel et al. | |
| 6,466,822 B1 | 10/2002 | Pless | |
| 6,473,568 B2 | 10/2002 | Kashiyama | |
| 6,473,639 B1 | 10/2002 | Fischell et al. | |
| 6,480,743 B1 | 11/2002 | Kirkpatrick et al. | |
| 6,484,059 B2 | 11/2002 | Gielen | |
| 6,487,450 B1 | 11/2002 | Chen | |
| 6,499,488 B1 | 12/2002 | Hunter et al. | |
| 6,505,075 B1 | 1/2003 | Weiner | |
| 6,507,755 B1 | 1/2003 | Gozani et al. | |
| 6,529,774 B1 | 3/2003 | Greene | |
| 6,539,263 B1 | 3/2003 | Schiff et al. | |
| 6,556,868 B2 | 4/2003 | Naritoku et al. | |
| 6,569,654 B2 | 5/2003 | Shastri et al. | |
| 6,591,138 B1 | 7/2003 | Fischell et al. | |
| 6,597,954 B1 | 7/2003 | Pless et al. | |
| 6,615,065 B1 | 9/2003 | Barrett et al. | |
| 6,622,048 B1 | 9/2003 | Mann et al. | |
| 6,633,780 B1 | 10/2003 | Berger | |

| | | |
|---|---|---|
| 6,647,296 B2 | 11/2003 | Fischell et al. |
| 6,665,562 B2 | 12/2003 | Gluckman et al. |
| 6,684,105 B2 | 1/2004 | Cohen et al. |
| 6,687,525 B2 | 2/2004 | Llinas et al. |
| 6,690,974 B2 | 2/2004 | Archer et al. |
| 6,708,064 B2 | 3/2004 | Rezai |
| 6,725,094 B2 | 4/2004 | Saberski |
| 6,731,978 B2 | 5/2004 | Olson et al. |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,907,296 B1 | 6/2005 | Doan et al. |
| 6,934,580 B1 | 8/2005 | Osorio et al. |
| 6,944,497 B2 | 9/2005 | Stypulkowski |
| 6,944,501 B1 | 9/2005 | Pless |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,065,412 B2 | 6/2006 | Swoyer |
| 7,107,097 B2 | 9/2006 | Stern et al. |
| 7,107,104 B2 | 9/2006 | Keravel et al. |
| 7,110,820 B2 | 9/2006 | Tcheng et al. |
| 7,146,217 B2 | 12/2006 | Firlik |
| 7,149,586 B2 | 12/2006 | Greenberg et al. |
| 2001/0051819 A1 | 12/2001 | Fischell et al. |
| 2002/0077670 A1 | 6/2002 | Archer |
| 2002/0087201 A1 | 7/2002 | Firlik et al. |
| 2002/0091419 A1 | 7/2002 | Firlik |
| 2002/0099412 A1 | 7/2002 | Fischell et al. |
| 2002/0169485 A1 | 11/2002 | Pless et al. |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0114886 A1 | 6/2003 | Gluckman et al. |
| 2003/0125772 A1 | 7/2003 | Olsen et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | DeCharms |
| 2004/0102828 A1 | 5/2004 | Lowry et al. |
| 2004/0111127 A1 | 6/2004 | Gliner et al. |
| 2004/0131998 A1 | 7/2004 | Marom et al. |
| 2004/0138550 A1 | 7/2004 | Hartlep et al. |
| 2004/0158298 A1 | 8/2004 | Gliner et al. |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst |
| 2006/0015153 A1 | 1/2006 | Gliner et al. |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |
| 2006/0241717 A1 | 10/2006 | Whitehurst et al. |
| 2009/0088827 A1* | 4/2009 | Tockman et al. ............ 607/123 |

FOREIGN PATENT DOCUMENTS

| | | |
|---|---|---|
| EP | 0214527 | 3/1987 |
| EP | 0319844 | 6/1989 |
| EP | 0998958 | 5/2000 |
| EP | 1145736 | 10/2001 |
| EP | 1180056 | 11/2003 |
| WO | WO 87-07511 | 12/1987 |
| WO | WO 94-07564 | 4/1994 |
| WO | WO 95-21591 | 8/1995 |
| WO | WO 98-06342 | 2/1998 |
| WO | 0119977 | 3/2001 |
| WO | WO 01-97906 | 12/2001 |
| WO | WO 02-09811 | 2/2002 |
| WO | WO 02-36003 | 5/2002 |
| WO | WO 02-38031 | 5/2002 |
| WO | WO 02-38217 | 5/2002 |
| WO | WO 03-043690 | 5/2003 |
| WO | WO 03-082402 | 10/2003 |

OTHER PUBLICATIONS

U.S. Appl. No. 11/254,060, filed Oct. 19, 2005, Wyler.
U.S. Appl. No. 11/254,240, filed Oct. 19, 2005, Wyler.
U.S. Appl. No. 11/255,187, filed Oct. 19, 2005, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/583,349, filed Oct. 18, 2006, Sloan.
U.S. Appl. No. 11/638,326, filed Dec. 12, 2006, Gliner et al.
Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).
Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).
Behrens, T. et al., "Non-invasive mapping of connections between human thalamus and cortex using diffusion imaging," Nature neuroscience, vol. 6 No. 7, pp. 750-757 (Jul. 2003).
Bel, S. and Bauer, B.L., "Dorsal col. Stimulation (DCS): Cost to Benefit Analysis," Acta Neurochirurgica, Suppl. 52, pp. 121-123 (1991).
Benabid, A.L. et al., "Chronic electrical stimulation of the ventralis intermedius nucleus of the thalamus as a treatment of movement disorders," J. Neurosurg., Apr. 1997, 86(4); 737; http:—www.ncbi.nlm.nih.gov; [accessed Nov. 18, 2003].
Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.
Bezard et al., "Cortical Stimulation and Epileptic Seizure: A Study of the Potential Risk in Primates," Neurosurgery, vol. 45, No. 2, Aug. 1999, 346-350.
Binder, J. M.D., "Functional Magnetic Resonance Imaging: Language Mapping," Neurosurgery Clinics of North America, vol. 8, No. 3, Jul. 1997, pp. 383-392.
Bluestone, Avraham Y. et al., "Three-dimensional optical tomography of hemodynamics in the human head," Optics Express, vol. 9, No. 6, pp: 272-286 (Sep. 10, 2001).
Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].
Burnett, Mark G. et al., "Diffuse optical measurement of blood flow, blood oxygenation, and metabolism in a human brain during sensorimotor cortex activation," Optics Letters, vol. 29, No. 15, pp: 1766-1768 (Aug. 1, 2004).

Bury, Scott et al., "The Effects of Behavioral Demand on Motor Cortical and Cerebellar Structural Plasticity After Brain Injury in Adult Rats," http://www.mcmaster.ca-inabis98-schallert-bury0827-two.html#introduction, 2 pages [Retrieved on Mar. 1, 2003].

Butefisch et al., "Mechanisms of use-dependent plasticity in the human motor cortex," Proc. Natl. Acad. Sci. USA, vol. 97, No. 7, pp. 3661-3665 (Mar. 2000).

Canavero, S. and Paolotti, R., "Extradural Motor Cortex Stimulation for Advanced Parkinson's Disease: Case Report," Movement Disorders, 15(1)169-171, 2000.

Cao, Yue et al., "Cortical Language Activation in Stroke Patients Recovering From Aphasia With Functional MRI," Stroke, vol. 30, pp: 2331-2340, Nov. 1999.

Cheun et al., "Differentiation of a Stem Cell Line Toward a Neuronal Phenotype," Int. J. Devl. Neuroscience, vol. 9, No. 4, pp. 391-404 (1991).

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Reorganization of the motor cortex in a patient with congenital hemiparesis and mirror movements," Neurology, vol. 55, pp. 129-131 (2000).

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

Classen et al., "Rapid Plasticity of Human Cortical Movement Representation Induced by Practice," The Journal of Neurophysiology, vol. 79, No. 2, pp. 1117-1123 (Feb. 1998).

CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].

Cohen et al., "Studies of Neuroplasticity With Transcranial Magnetic Stimulation," The Journal of Clinical Neurophysiology, vol. 15, No. 4 (1998).

Cramer et al., "Use of Functional MRI to Guide Decisions in a clinical Stroke Trial," Stroke, Journal of the American Heart Association, May 2005, pp. e50-e52, American Heart Association, Dallas TX.

Cramer, S.C. and Bastings, E.P., "Mapping clinically relevant plasticity after stroke," Neuropharmacology vol. 19, No. 5, pp. 842-851 (Apr. 2000).

Cytokines Web Clinical Significance, Cytokines Web, 2 pages, URL: http:—cmbi.bjmu.edu.cn-cmbidata-cgf-CGF_Database-cytweb-roles-index.html [Retrieved on Sep. 2, 2005].

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

De Ridder, Dirk et al., "Magnetic and electrical stimulation of the auditory cortex for intractable tinnitus," Journal Neurosurg., vol. 100, pp: 560-564, (Mar. 2004).

Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.

Ding, Yuemin et al., "Neural Plasticity After Spinal Cord Injury," Current Pharmaceutical Design vol. 11, No. 11, pp: 1441-1450, Abstract Only, 1 page (Apr. 2005).

Duncan, Pamela W. et al., "Defining post-stroke recovery: implications for design and interpretation of drug trials," Neuropharmacology vol. 39, pp. 835-841 (2000).

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93:873-875 (2000).

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Fregni, Felipe et al., "Anodal Transcranial Direct Current Stimulation of Prefrontal Cortex Enhances Working Memory," Experimental Brain Research vol. 166, No. 1, pp: 23-30 (Sep. 2005).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371-377 (1990).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Haglund, Michael M. et al., "Optical imaging of epileptiform and functional activity in human cerebral cortex," Nature, Aug. 20, 1992, pp. 668-671, vol. 358, Nature Publishing Group.

Hayakawa, Toshiji et al., "Changes in Cerebral Oxygenation and Hemodynamics During Obstructive Sleep Apneas," Chest, vol. 109, pp. 916-921 (1996).

Hodge, Jr., C.J. and Boakye, M., "Biological Plasticity: The Future of Science in Neurosurgery," Neurosurgery, vol. 48, No. 1 (Jan. 2001).

Hoshi, Yoko et al., "Detection of dynamic changes in cerebral oxygenation coupled to neuronal function during mental work in a man," Neuroscience Letters, vol. 150, pp: 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., http://www.iss.com-Products-imagent_fmri.html, 1 page [Retrieved on Oct. 14, 2005].

Huang, Ying-Zu et al., "Theta Burst Stimulation of the Human Motor Cortex," Neuron, vol. 45, pp. 201-206 (Jan. 20, 2005).

Hummel, Friedhelm et al., "Effects of non-invasive cortical stimulation on skilled motor function in chronic stroke," Brain Advance Access, pp. 1-10, (Jan. 5, 2005).

Imagent™ Functional Brain Imaging System, ISS, Inc., http://www.iss.com-Products-imagent.html, 2 pages [Retrieved on Oct. 14, 2005].

Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kauhanen et al., "Domains and Determinants of Quality of Life After Stroke Caused by Brain Infarction," Arch. Phys. Med. Rehabil., vol. 81, pp. 1541-1546 (Dec. 2000).

Kelly-Spratt, K. "Transfection of PC-12 cells: a model system for primary neuronal cells," Qiagen News, Customer application article, www.qiagen.com, Issue 4, 1998, 2 pages.

Keyvani, Kathy et al., "Suppression of proteasome C2 contralateral to ischemic lesions in rat brain," Brain Research, vol. 858, pp: 386-392, 2000.

Kilgard, Michael et al., "Cortical Map Reorganization Enabled by Nucleus Basalis Activity," Science, vol. 279 pp. 1714-1717 (Mar. 13, 1998).

Kimura, K. et al., "Electrically induced neurite outgrowth of PC12 cells on the electrode surface," Entrez PubMed, http://www.ncbi.nlm.nih.gov/entrez/query.fcgi?db=pubmed&cmd=Retrieve&dopt=Abstract, 1 page.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kopell et al., "The Continuing Evolution of Psychiatric Neurosurgery," CNS Spectrums, vol. 5, No. 10, pp. 20-31 (Oct. 2000).

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias, BioChemistry of PD, http://www.mayo.edu-fdp-pd-info-dyskinesias.htm [Retrieved on Dec. 22, 2005].

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G. et al., "A sham stimulation-controlled trial of rTMS of the unaffected hemisphere in stroke patients," Neurology, vol. 64, pp. 1802-1804 (2005).

Martin et al., "Transcranial Magnetic Stimulation as a Complementary Treatment for Aphasia," Semin Speech Language, vol. 25, pp: 181-191 (2004) Abstract Only- 1 page.

Martinez et al., "Motor hand recovery after stroke Prognostic yield of early transcranial magnetic stimulation," Electromyography. Clin. Neurophysiology, vol, 39, pp. 405-410 (1999).

Mendonca, A.C., "Directly applied low intensity direct electric current enhances peripheral nerve regeneration in rats," Journal of Neuroscience Methods, 2003, vol. 129, pp. 183-190.

Meyerson, B.A. et al., "Motor Cortex Stimulation as Treatment of Trigeminal Neuropathic Pain", Acta Neurochirurgica Supplementum, vol. 58, pp: 150-153 (1993).

Misawa et al., "Low-frequency transcranial magnetic stimulation for epilepsia partialis continua due to cortical dysplasia," Journal of the Neurological Sciences, vol. 234, 2005, pp. 37-39.

Montgomery, "Thalamic Stimulation," Neuroscience Pathways, The Cleveland Clinic Foundation, 2 pages.

Motamedi et al., "Optimizing Parameters for Terminating Cortical Afterdischarges with Pulse Stimulation," Epilepsia 43(8):836-846, 2002, Blackwell Publishing, Inc.

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Nitsche, Michael A. et al., "Level of action of cathodal DC opographyn induced inhibition of the human motor cortex," Dec. 2, 2002, Clinical Neurophysiology 114 (2003) 600-604.

Nudo, Randolph J. et al., "Recovery after damage to motor cortical areas," Current Opinion in Neurobiology, vol. 9, Issue 6, pp: 740-747, Dec. 1, 1999.

Oliveri et al., "Paired transcranial magnetic stimulation protocols reveal a pattern of inhibition and facilitation in the human parietal cortex," The Journal of Physiology, 529.2, pp. 461-468 (2000).

Panchanathan, Sethuraman et al., "Rehabilitation of patients with hemispatial neglect using visual-haptic feedback in Virtual reality environment," http://www.public.asu.edu-~tmcdani-publications. htm, 5 pages [Retrieved on Dec. 22, 2005].

Pascual-Leone et al., "Study and Modulation of Human Cortical Excitability With Transcranial Magnetic Stimulation," Journal of Clinical Neurophysiology, 1998, vol. 15, No. 4, pp. 333-343.

Pascual-Leone et al., "Transcranial magnetic stimulation and neuroplasticity," Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," on Wisconsin Alumni Magazine, Summer 2003, http://www.uwalumni.com-onwisconsin-2003_summer-research.html, 1 page [Retrieved on Dec. 22, 2005].

Politis, M. J., "Mammalian Optic Nerve Regeneration Following the Application of Electric Fields," The Journal of Trauma, Nov. 1988, vol. 28, No. 11, pp. 1548-1552.

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2423-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annual Review of Neuroscience 23:393-415 (2000).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

Schulz et al., "Localization of Epileptic Auras Induced on Stimulation by Subdural Electrodes," Epilepsia, Dec. 1997, vol. 38, Issue 12, pp. 1321-1329.

SCIRun, Scientific Computing and Imaging Institute. http://www.sofware.sci.utah.edu-scirun.html, 2 pages [Retrieved on Jul. 24, 2005].

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Sioutos et al. Continuous Regional Cerebral Cortical Blood Flow Monitoring in Head-injured Patients, Neurosurgery, vol. 36, No. 5, May 1995, pp. 943-949.

Stefan et al., "Introduction of plasticity in the human motor cortex by paired associative stimulation," Brain, vol. 123, No. 3, pp. 572-584 (Mar. 2000).

Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.

Strangman, Gary et al., "A Quantitative Comparison of Simultaneous BOLD fMRI and NIRS Recordings during Functional Brain Activation," NeuroImage, vol. 17, pp: 719-731 (2002).

Strangman, Gary et al., "Factors affecting the accuracy of near-infrared spectroscopy concentration calculations for focal changes in oxygenation parameters," NeuroImage, vol. 18, pp: 865-879 (2003).

Strangman, Gary et al., "Non-Invasive Neuroimaging Using Near-Infrared Light," Biological Psychiatry, vol. 52, pp: 679-693 (2002).

Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

Taga, Gentaro et al., ",Brain imaging in awake infants by near-infrared optical topogrpahy," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research, Electrical Geodesics, Inc., http://www.egi.com/ges250r_n.html, 3 pages [Retrieved on Aug. 25, 2005].

The INVOS Cerebral Oximeter, Somanetics, http://www.somanetics.net/invos.htm, 1 page [retrieved from the Internet on Dec. 22, 2005].

The National Institutes of Health (NIH) Consensus Development Program, "Surgery for Epilepsy," National Institutes of Health Consensus Development conference Statement, Mar. 19-21, 1990, 16 pages.

Theoret, Hugo et al., "Exploring Paradoxical Functional Facilitation with TMS," Supplements to Clinical Neurophysiology, vol. 56, pp: 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp: 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp: 801-815 (Apr. 2000).

Tractography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp: 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", PACE, vol. 14, pp: 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Vanderkooy et al., "Resolution Below the Least Significant Bit in Digital Systems with Dither," JAES, Mar. 1984, vol. 32, No. 3, pp. 106-113.

Van Der Lee et al., "The Intra- and lnterrater Reliability of the Action Research Arm Test: A Practical Test of Upper Extremity Function in Patients With Stroke," Arch. Phys. Med. Rehabil., vol. 82 pp. 14-19 (Jan. 2001).

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of Hippocampai Foci," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Walker-Batson et al., "Amphetamine Paired With Physical Therapy Accelerates Motor Recovery After Stroke," Stroke, vol. 26, No. 12, pp. 2254-2259 (1995).

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005 AANS.org, http://www.aans.org/Library/Article.aspx?ArticleId=24934, 2 pages.

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Yokoh, Arika et al., "Intermittent versus continuous brain retraction," Journal of Neurosurgery, vol. 58, pp: 918-923 (Jun. 1983).

Ziemann et al., "Modulation of Plasticity in Human Motor Cortex after Forearm Ischemic Nerve Block," The Journal of Neuroscience 18(3):1115-1123 (Feb. 1998).

U.S. Appl. No. 60/325,872, filed Sep. 28, 2001.

U.S. Appl. No. 60/325,978, filed Sep. 28, 2001.

U.S. Appl. No. 09/978,134, filed Oct. 15, 2001.

International Search Report for Application No. PCT/US2002/32695; Applicant: Vertis Neuroscience, Inc.; Dec. 27, 2002; 9 pgs; European Patent Office.

International Search Report for PCT/US2003/09211 dated Sep. 28, 2005.

* cited by examiner

550

560

ELECTRODE GEOMETRIES FOR EFFICIENT NEURAL STIMULATION

CROSS-REFERENCE TO RELATED APPLICATION

This application is a division of U.S. patent application Ser. No. 10/112,301, filed Mar. 28, 2002, and entitled "Electrode Geometries For Efficient Neural Stimulation," incorporated herein by reference in its entirety, and which relates to and incorporates by reference U.S. patent application Ser. No. 09/978,134, entitled "Systems and Methods for Automatically Optimizing Stimulus Parameters and Electrode Configurations for Neuro-Stimulators," filed on Oct. 15, 2001.

TECHNICAL FIELD

The present invention relates generally to electrodes suitable for neural stimulation. More particularly, the present invention includes a variety of electrode geometries or designs directed toward enhancing the efficiency of neural stimulation, and/or increasing electrode reliability.

BACKGROUND

A variety of medical procedures involve electrically monitoring and/or stimulating neural tissue, such as regions of the cortex or spinal cord. For example, epileptogenic foci localization may be accomplished through cortical monitoring procedures; and various neurologically based pain conditions may be treated with cortical or spinal stimulation. Electrical signals may be exchanged with neural tissue through an electrode that includes a set of electrically conductive contacts.

The effectiveness of a neural stimulation procedure may be related to the electric field distribution produced by or associated with an electrode employed in the procedure. In general, the electric or stimulation field distribution depends upon a) electrode design; b) the particular electrode contacts to which electrical stimulation signals are applied; and c) the magnitudes and polarities of applied stimulation signals. An electrode's design encompasses the structure and spatial organization of its contacts, and/or the as-manufactured electrical couplings thereto. In order to maximize the likelihood that neural stimulation will be effective, an electrode design should be capable of producing an intended or desired type of stimulation field distribution. Depending upon stimulation requirements, an electrode design capable of providing flexibility with respect to manners in which stimulation field distributions may be established, configured, or tailored may be advantageous.

Neural microelectrodes are designed for micro-scale neural monitoring and/or stimulation, that is, highly localized signal exchange with very small neural populations or single neurons. Neural microelectrode types may include patch clamp or pipette microelectrodes; etched and/or micromachined needle electrodes or probes; and annular microelectrodes. An annular microelectrode capable of preferentially stimulating a single neuron soma is described in U.S. Pat. No. 5,411,540. Unlike the procedures disclosed in U.S. Pat. No. 5,411,540, many neural monitoring and/or stimulation procedures involve signal exchange with sizeable neural populations, i.e., hundreds, thousands, many thousands, or even millions of neurons. The microelectrodes disclosed in U.S. Pat. No. 5,411,540 accordingly have very limited applicability to such procedures.

Neural microelectrode arrays include multiple neural microelectrodes organized in a regular pattern and formed or mounted upon a substrate. Although a neural microelectrode array may be capable of monitoring and/or stimulating a larger neural population than an individual neural microelectrode, such an array may be undesirably complex and/or expensive from a manufacturing standpoint.

Grid electrodes may facilitate macro-scale neural monitoring and/or stimulation, that is, neural tissue monitoring and/or stimulation involving hundreds, thousands, hundreds of thousands, or perhaps millions of neurons. FIG. 1 is a plan view of a conventional grid electrode 100, which comprises a plurality of contacts 110 uniformly arranged in an array or a set of generally rectangular or rectilinear patterns; a lead wire 120 coupled to each contact 110; one or more electrode leads 130 into which lead wires 120 may be organized and/or routed; and a medium, substrate, or backing 140 upon and/or within which the contacts 110, the lead wires 120, and possibly portions of the electrode leads 140 reside. Conventional grid electrodes 100 are available from Ad-Tech Medical Instrument Corporation of Racine, Wisc. In general, the contacts 110, the lead wires 120, one or more portions of the electrode leads 130, and the substrate 140 are formed from biocompatible materials in a manner readily understood by those skilled in the art.

Conventional grid electrodes 100 may include a significant number of contacts 110. Such grid electrodes 100 maintain a one-to-one ratio between the number of contacts 110 and the number of lead wires 120. Thus, a conventional eight-by-eight grid electrode 100 having sixty-four contacts 110 includes sixty-four lead wires 120. Any given lead wire 120 may be coupled to a desired stimulation signal via an external signal routing interface that is connected to a stimulation signal source in a manner readily understood by those skilled in the art. Conventional grid electrodes 100 may facilitate a limited degree of simulation field configurability through selective coupling between specific contacts 110 and particular stimulation signals.

An electrode implant procedure may be highly invasive from a surgical standpoint, possibly requiring, for example, a craniotomy. Electrode reliability is therefore of paramount importance. Unfortunately, the large number of lead wires 120 resulting from a grid electrode's one-to-one contact to lead wire ratio increases the complexity and decreases the reliability of an electrode lead 130. Thus, conventional grid electrode arrays may not be suitable for use in procedures that require implanted electrodes.

DETAILED DESCRIPTION

The following discussion is presented to enable a person skilled in the art to make and use the invention. The general principles described herein may be applied to embodiments and applications other than those detailed below without departing from the spirit and scope of the present invention as defined by the appended claims. The present invention is not intended to be limited to the embodiments shown, but is to be accorded the widest scope consistent with the principles and features disclosed herein.

The present invention comprises a variety of electrode designs or geometries that may provide enhanced neural stimulation efficiency. Enhanced neural stimulation efficiency may be particularly valuable or important when stimulation is directed toward inducing and/or enhancing neuroplasticity for neural function rehabilitation and/or other purposes. The present invention additionally comprises electrode designs that may decrease electrode complexity and thus increase electrode reliability. Increased electrode reliability may be particularly important in neural stimulation situations because electrodes may be implanted on a permanent or long term basis, possibly through a significantly invasive surgical implant procedure. The use of electrodes for intracranial neural stimulation is described in U.S. patent application Ser. No. 09/978,134, entitled "Systems and Methods for Automatically Optimizing Stimulus Parameters and Electrode Configurations for Neuro-Stimulators," filed on Oct. 15, 2001.

Depending upon neural stimulation requirements and/or electrode embodiment details, electrodes constructed in accordance with the present invention may selectively employ concentric contacts; arc and/or generally arc shaped contacts; variations in contact number, positioning, spacing, and/or distribution; variations in contact shape, area, and/or periphery; and/or conductive on-electrode links or interconnections between particular contacts to provide an intended type of stimulation field distribution, as described in detail hereafter.

Figure 2A:
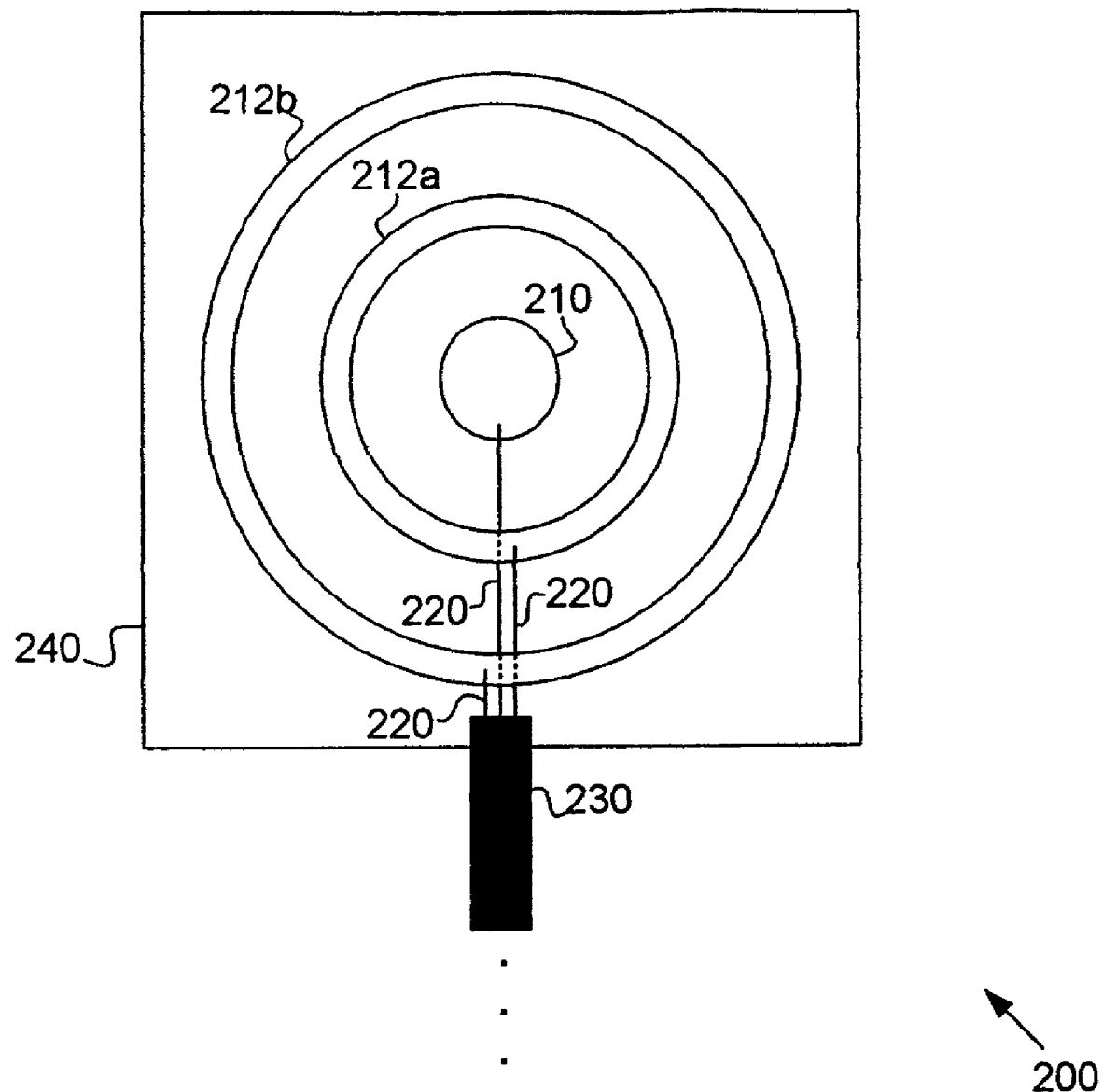
FIG. 2A is a plan view of an annular electrode configured for macro-scale neural stimulation according to an embodiment of the invention.

FIG. 2A is a plan view of an annular electrode 200 configured for macro-scale neural stimulation according to an embodiment of the present invention. The annular electrode 200 comprises a central contact 210 and one or more annular contacts 212a, 212b that encircle the central contact 210. The electrode 200 also includes a lead wire 220 corresponding to each contact 210, 212a, 212b; one or more electrode leads 230 into which lead wires 220 may be grouped, organized, and/or routed; and a medium, substrate, or backing 240. The central contact 210, the annular contacts 212a, 212b, the lead wires 220, and possibly portions of the electrode leads 230 are carried by the substrate 240. The contacts 210, 212a, 212b, the lead wires 220, one or more portions of the electrode leads 230, and the substrate 240 are formed from biocompatible materials known to persons skilled in the art. Suitable materials for the contacts 210, 212a, 212b include stainless steel, platinum, platinum-iridium, iridium oxide, or gold. It will be appreciated that the contacts 210, 212a, 212b can comprise other materials and/or coatings.

The substrate 240 of the annular electrode may be soft and/or flexible, such that it may readily conform to a wide variety of neural tissue surfaces. Each contact 210, 212a, 212b is sufficiently large that the annular electrode 200 may deliver stimulation to a macro-scale neural tissue region, which may include a large number of neural cell bodies. In one embodiment, a surface area enclosed by an outermost annular contact 212b is many times larger than the surface area associated with a single neural cell body, even when considering large types of neurons such as pyramidal neurons. The annular electrode 200 may be suitable for delivering stimulation to a region of the cerebral cortex; for example, the electrode 200 may be implanted proximate to a cortical region associated with controlling a particular type of mental or physical function.

Figure 2B:
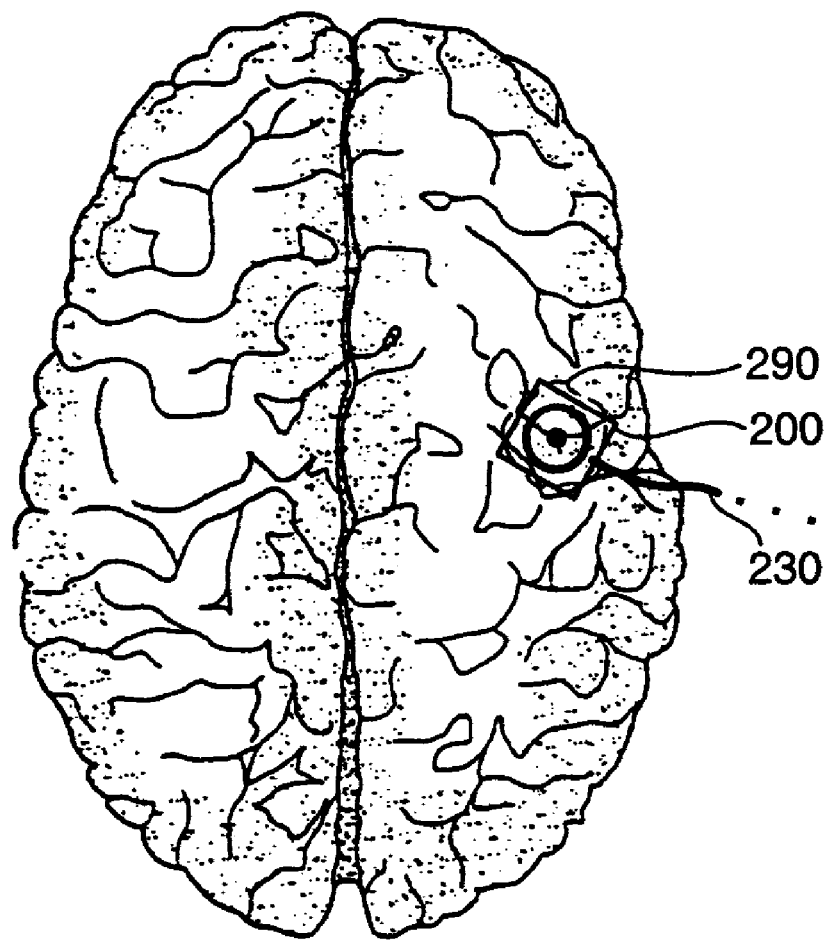
FIG. 2B is a plan view of an annular electrode positioned upon a neural tissue surface region and configured to provide macro-scale stimulation to a neural tissue within and/or beneath the neural tissue surface region according to an embodiment of the invention.

FIG. 2B is a plan view of an annular electrode 200 positioned upon a neural tissue surface region 290 and configured to provide macro-scale stimulation to neural tissue within and/or beneath the neural tissue surface region 290 according to an embodiment of the invention. The annular electrode 200 may be positioned with respect to a given neural tissue surface region 290 through a surgical implant procedure, such as described in U.S. patent application Ser. No. 09/978,134. The annular electrode 200 may be implanted, for example, subdurally to deliver electrical stimulation to a particular portion of the cerebral cortex. An electrode lead 230 may be positioned such that it minimally contacts and/or impacts neural tissue, and may be routed away from neural tissue via an opening in the skull through which the annular electrode 200 was implanted. A stimulation field distribution produced by an annular electrode 200 may be characterized by a high degree of radial uniformity, which may be desirable in certain neural stimulation applications.

Figure 3A:
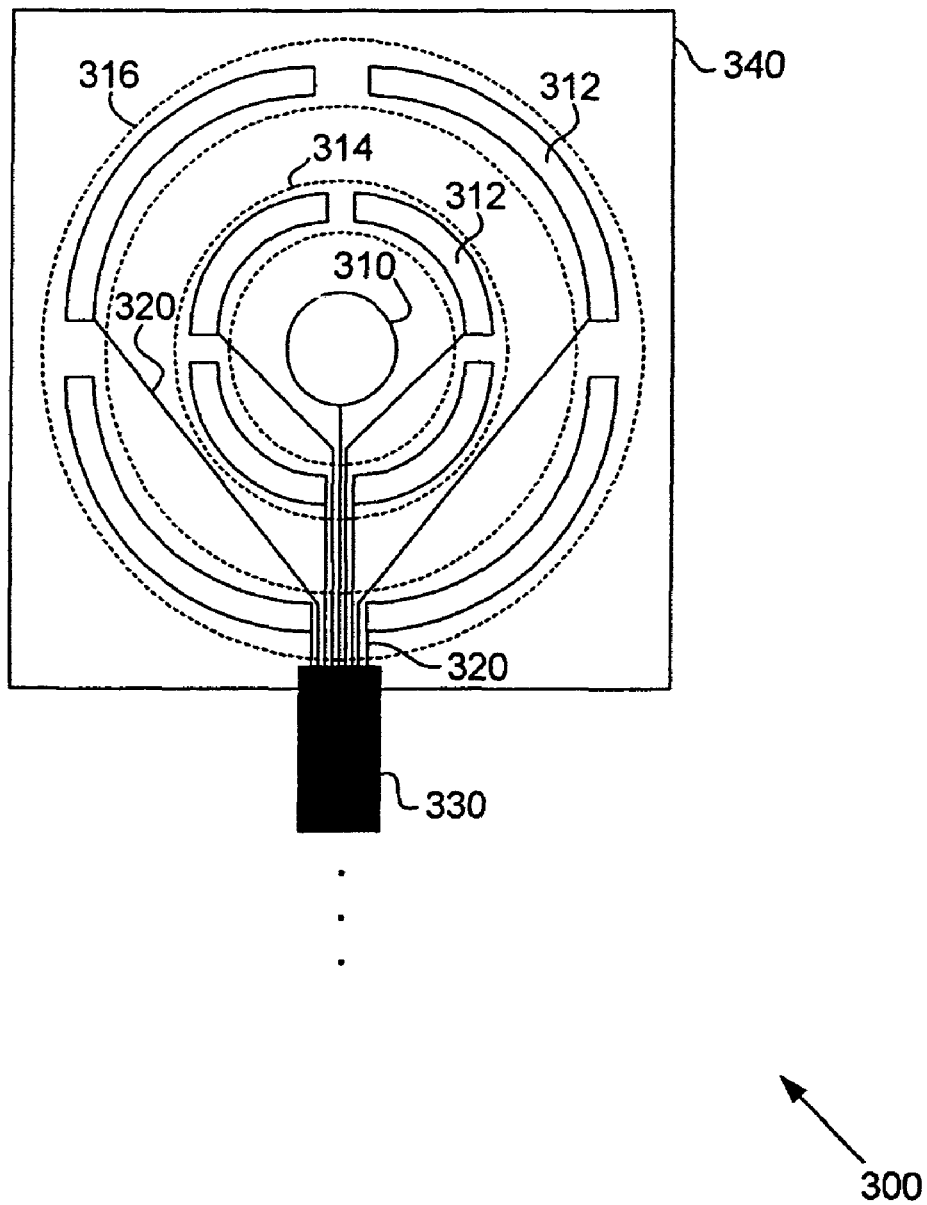
FIG. 3A is a plan view of an arc electrode according to an embodiment of the invention.
Figure 3B:
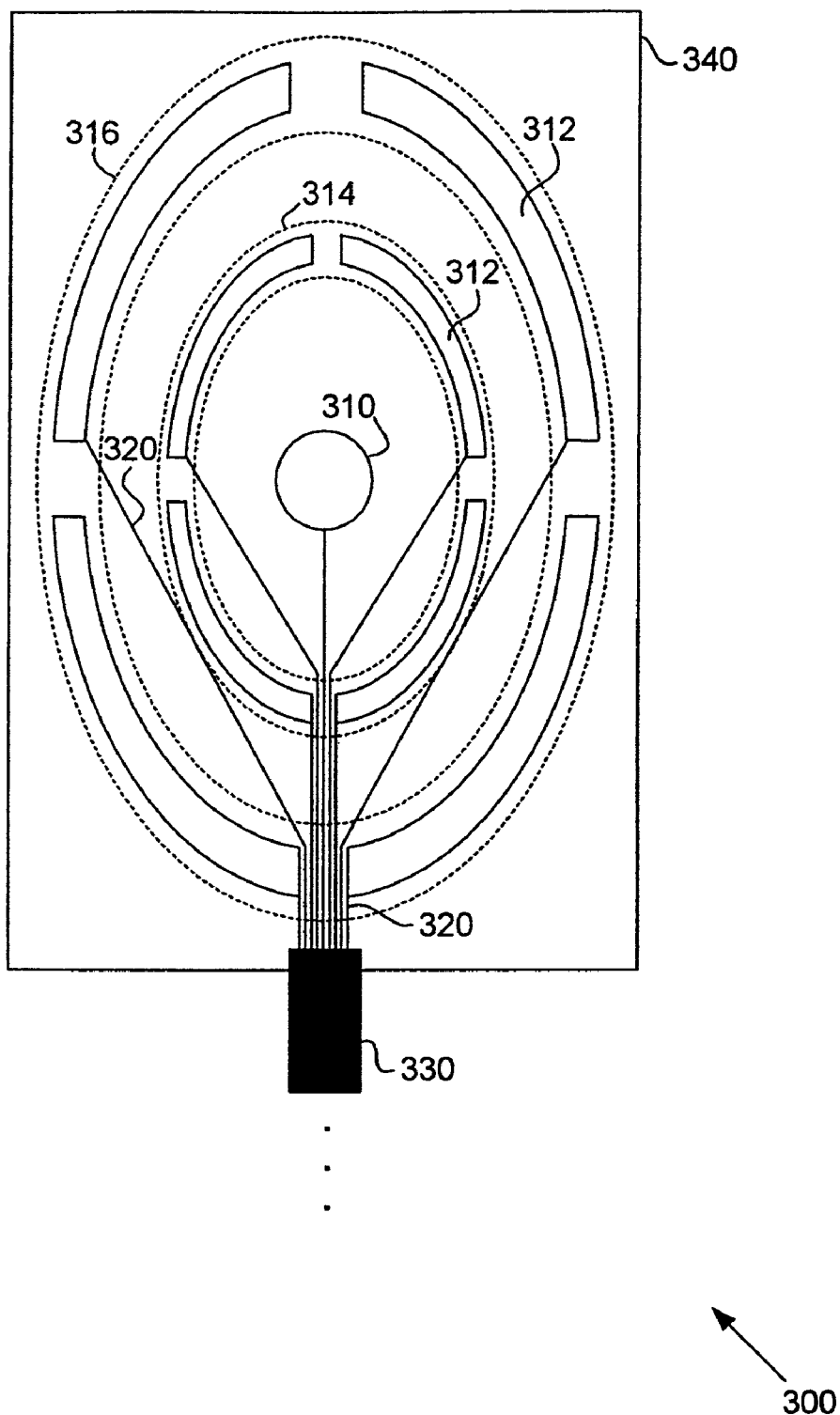
FIG. 3B is a plan view of an arc electrode according to another embodiment of the invention.

FIG. 3 is a plan view of an arc electrode 300 according to an embodiment of the invention. In one embodiment, the arc electrode 300 comprises a central contact 310, which may be disk-shaped, and a set of arc contacts 312 concentrically and/or peripherally positioned or arranged relative to the central contact 310. The electrode 300 further comprises lead wires 320 coupled to the central and arc contacts 310, 312; an electrode lead 330 into which lead wires 320 may be grouped, organized, and/or routed; and a medium, substrate, or backing 340. As with the electrode 200, the contacts 310, 312, portions of the lead wires 320, and possibly portions of the electrode lead 330 are carried by the substrate 340.

The central and each arc contact 310, 312 may comprise a compositionally stable, biologically compatible, electrically conductive material such as Stainless Steel, Platinum, Platinum-Iridium, Iridium Oxide, Gold, and/or other materials and/or coatings. The arc electrode 300 may be manufactured using conventional electrode manufacturing processes or techniques.

An arc contact 312 may exhibit a curved, bent, or arc-like shape, and may be characterized by a radius of curvature and an arc length. Depending upon the requirements of the stimulation field, the number, curvature, length, and/or position of the arcs may vary. In alternate embodiments, one or more arc contacts 312 may exhibit v-like or other types of curved or angled shapes.

Arc contacts 312 may be grouped or organized into particular patterns, which may be generally circular, elliptical, or otherwise shaped. Any given arc contact pattern may be positioned or oriented in a predetermined manner with respect to the central contact 310 and/or other contact patterns. In the embodiment shown in FIG. 3A, the arc contacts 312 are grouped into a first circular pattern 314 that generally surrounds the central contact 310; and a second circular pattern 316 that generally surrounds the first circular pattern 314. In the embodiment shown in FIG. 3B, the arc contacts 312 are grouped into an elliptical pattern. Those skilled in the art will understand that additional, fewer, and/or other types of arc contact patterns are possible in other embodiments.

The central contact 310 and each arc contact 312 may be coupled to corresponding lead wires 320. Any given lead wire 320 may be coupled to a particular stimulation signal at a stimulation signal source. Thus, within the first and/or second circular patterns 314, 316, successively positioned arc contacts 312 may be coupled to stimulation signals having identical or different magnitudes, biases, and/or temporal characteristics. In an analogous manner, arc contacts 312 that exhibit a given positional correspondence from one circular pattern 314, 316 to another may be coupled to stimulation signals having identical or different magnitudes, biases, and/or temporal characteristics. Hence, an arc electrode 300 constructed in accordance with the present invention may be configured to provide a wide variety of stimulation field distributions.

The present invention encompasses arc electrode embodiments beyond those described above. For example, an arc electrode 300 may omit the central contact 310, include additional or fewer arc contacts 312, and/or include one or more conventional annular contacts 112. As another example, an arc electrode 300 may include a centrally positioned contact grid in place of the central contact 310, in which case individual contacts within the contact grid may be coupled to one or more particular stimulation signals provided by a stimulation signal source. As yet another example, an arc electrode 300 may comprise one or more arc contacts 312 positioned in one or more non-concentric manners. Any given embodiment may be selected in accordance with stimulation field distribution requirements associated with a given neural stimulation situation.

In addition to arc electrode embodiments 300 such as those described above, the present invention also encompasses a variety of grid-like and/or other types of multi-contact electrode embodiments. In accordance with the present invention, one manner of affecting an electrical or stimulation field distribution is through nonuniform contact distribution, separation, or pitch. The description hereafter details various multi-contact electrode embodiments that may selectively exploit nonuniform contact separation to provide or approximate a desired or intended type of stimulation field distribution. Relative to various electrode embodiments described hereafter, like and/or analogous elements may be indicated with like reference numbers to aid understanding.

Figure 4A:
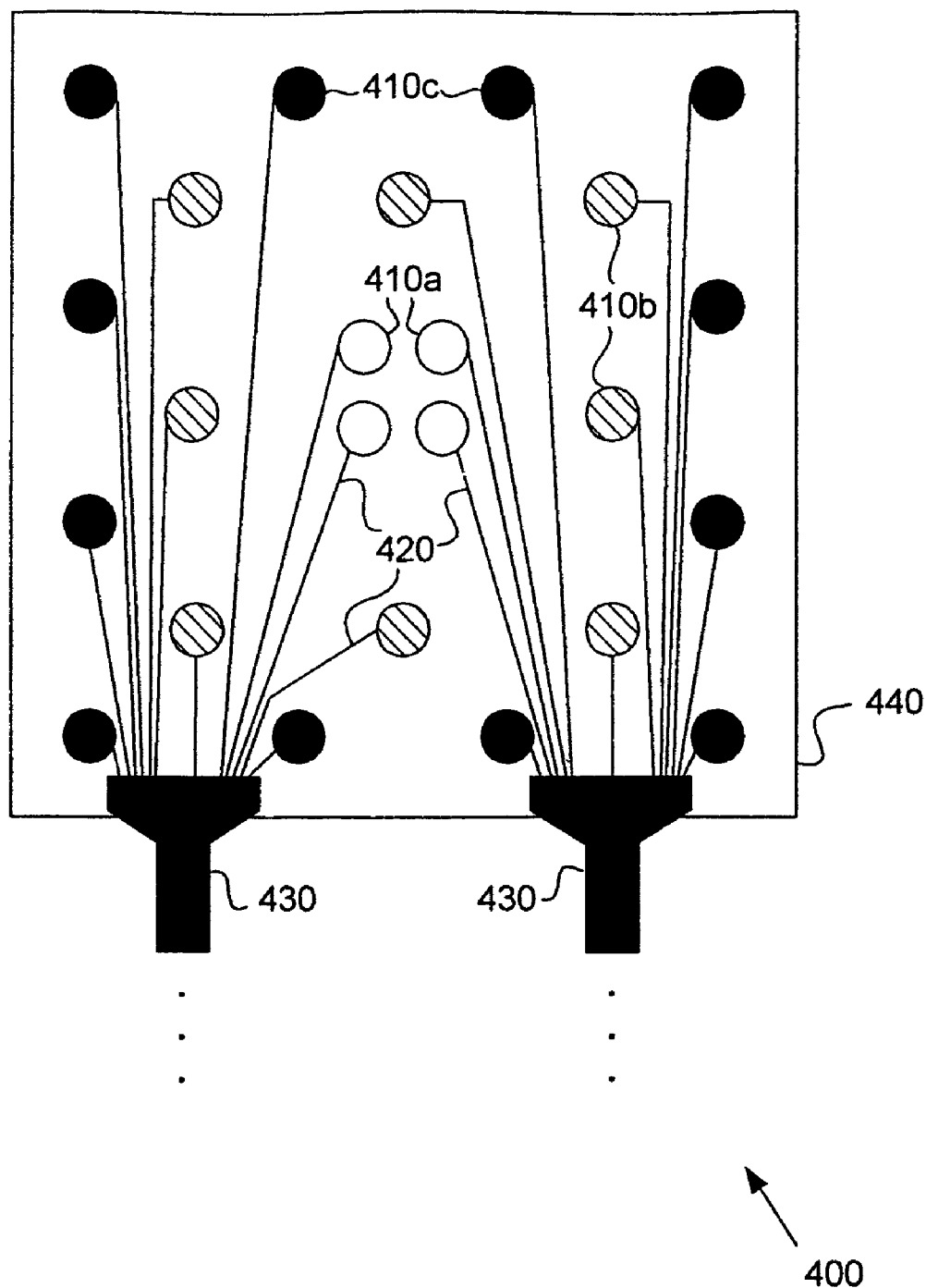
FIG. 4A is a plan view of an electrode exhibiting nonuniform contact separation according to an embodiment of the invention.

FIG. 4A is a plan view of an electrode 400 having nonuniform or uneven contact distribution, separation, or spacing according to an embodiment of the invention. In one embodiment, such an electrode 400 comprises a plurality of disk-shaped contacts 410a, 410b, 410c; a lead wire 420 coupled to each contact 410; a set of electrode leads 430 into which lead wires 420 may be organized and/or routed; and a medium, substrate, or backing 440 that carries the contacts 410a, 410b, 410c, the lead wires 420, and portions of the electrode leads 430. The contacts 410a-c can have other shapes in addition to or in lieu of disk shapes. The lead wires 420, one or more portions of the electrode leads 430, and the substrate 440 may be formed from biocompatible materials known in the art. Additionally, the contacts 410a-c may comprise a biologically compatible, electrically conductive material in a manner identical or analogous to that described above.

Relative to any given electrode embodiment, one or more contact organizational patterns may be defined. Depending upon embodiment details, the spacing between the contacts 410a-c within a subset of contacts may be nonuniform, and/or the spacing or separation between sets of contacts may be nonuniform. As such, the spacing between contacts in a pattern may be nonuniform, and/or the spacing between patterns of contacts may be nonuniform. In FIG. 4A, the contacts 410a are organized in accordance with a first pattern or distribution (shown unshaded); the contacts 410b are organized in accordance with a second pattern or distribution (shown crosshatched); and the contacts 410c are organized in accordance with a third pattern (shown in solid). The center-to-center or equivalent spacing between the contacts 410a organized in accordance with the first pattern is less than that of the contacts 410b, 410c organized in accordance with the second and third patterns. In addition, the distance between a border or edge corresponding to the first pattern and an equivalent type of border or edge corresponding to the second pattern differs from the distance between a border or edge corresponding to the second pattern and an equivalent type of border or edge corresponding to the third pattern. Thus, the distribution or spatial density of the contacts 410a-c may vary across the surface of an electrode 400 constructed in accordance with the present invention.

Other types of contact organizations or patterns may be defined with respect to any given embodiment and/or alternate embodiments. Moreover, any given contact organizational pattern may appear multiple times in the context of a single embodiment. The spatial distribution or density of contacts 410a-c within a contact organizational pattern may be nonuniform, and/or the spatial separation between particular contact organizational patterns may vary across an electrode's surface. Furthermore, a contact distribution pattern may be defined and/or employed based upon particular types of stimulation signals that may be applied to some or all contacts 410a-c within the pattern.

Figure 4B:
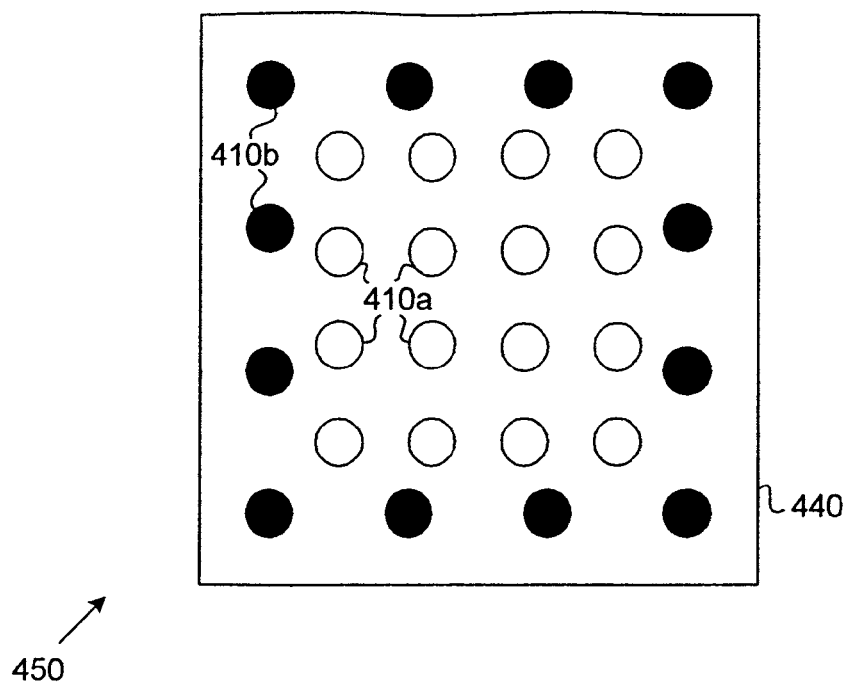
FIG. 4B is a plan view of an electrode exhibiting nonuniform contact separation according to another embodiment of the invention.

FIG. 4B is a plan view of an electrode 450 having nonuniform contact separation according to another embodiment of the invention. The electrode 450 shown in FIG. 4B may comprise identical and/or analogous types of elements as those shown in FIG. 4A, such that the number and/or positioning of such elements may differ in accordance with a contact organization scheme. In FIG. 4B, the contacts 410a are organized in accordance with a first pattern or distribution (shown unshaded), and the contacts 410b are organized in accordance with a second pattern (shown in solid). To simplify understanding, individual lead wires and an electrode lead are not shown in FIG. 4B. Notwithstanding, each contact 410a, 410b may be coupled to a corresponding lead wire, and lead wires may be organized and/or grouped into an electrode lead in a manner identical or generally analogous to that shown in FIG. 4A. Each element of the electrode 450 may be implemented using biocompatible materials.

As shown in FIG. 4B, the spatial density of the contacts 410a, 410b varies across the surface of the electrode 450. In particular, the center-to-center or equivalent spacing between any two contacts 410a organized in accordance with the first pattern differs from the center-to-center spacing between a contact 410a organized in accordance with the first pattern and a contact 410b organized in accordance with the second pattern.

Figure 4C:
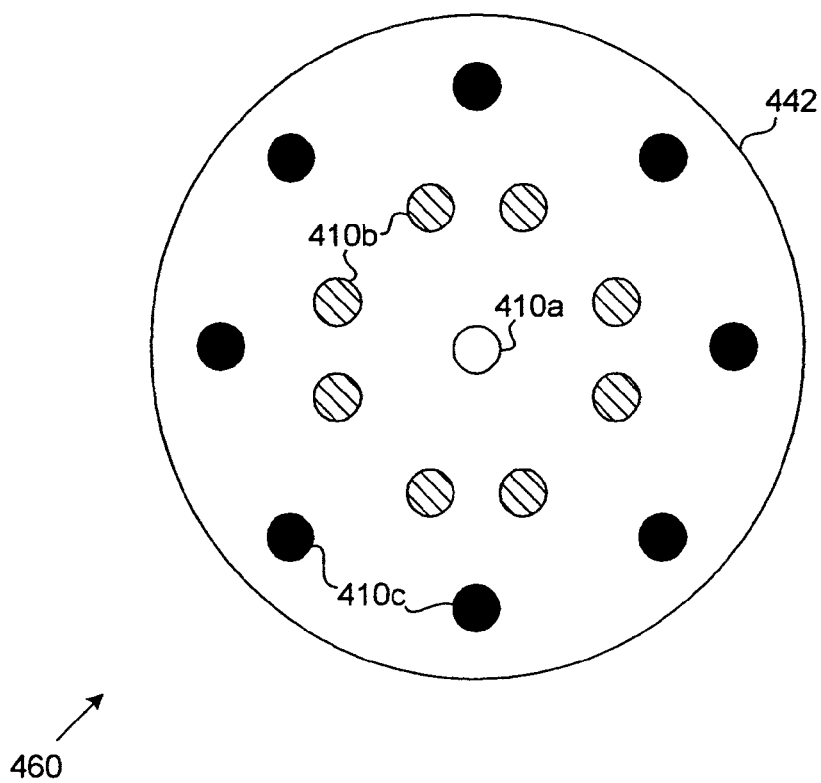
FIG. 4C is a plan view of a circular multi-contact electrode exhibiting nonuniform contact separation according to an embodiment of the invention.

FIG. 4C is a plan view of a circular multi-contact electrode 460 having nonuniform contact separation according to an embodiment of the invention. In the embodiment shown, the circular multi-contact electrode 460 comprises a plurality of the contacts 410a-c that reside upon and/or within a generally circular substrate, medium, or backing 442. As in FIG. 4B, individual lead wires and an electrode lead are not indicated in FIG. 4C to simplify understanding. Notwithstanding, each contact 410a-c may be coupled to a corresponding lead wire, and lead wires may be organized and/or grouped into an electrode lead in a manner identical, essentially identical, or analogous to that shown in FIG. 4A; and each element of the circular multi-contact electrode 460 may be implemented using conventional biocompatible materials, in a manner previously described. In FIG. 4C, a contact 410a organized in accordance with a first pattern is shown unshaded. Contacts 410b organized in accordance with a second pattern are shown cross-hatched, and contacts 410c organized in accordance with a third pattern are shown in black. In accordance with the present invention, the spatial distribution of the contacts 410a-c in FIG. 4C is nonuniform across the electrode 460.

In various embodiments, the separation distance between or spatial distribution of the particular contacts 410a-c and/or contact organizational patterns may be a function of distance from a set of the reference contacts 410a-c and/or reference contact organizational patterns. Thus, in one embodiment, the contacts 410a-c organized within any given organizational pattern may exhibit a uniform contact to contact separation distance, whereas separation distances between radially successive contact organizational patterns may increase or decrease with distance from a centrally-positioned contact organizational pattern.

Figure 1:
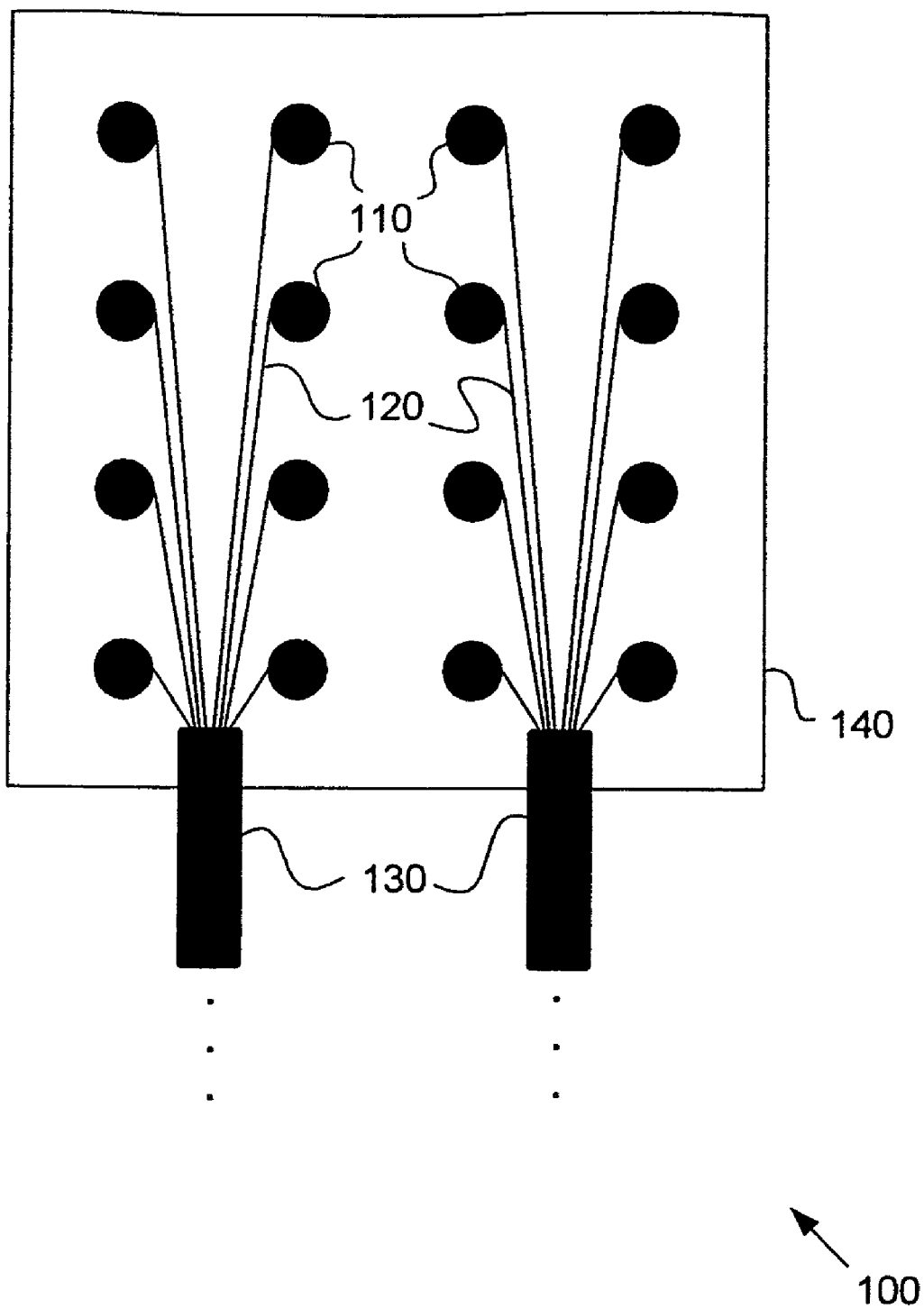
FIG. 1 is a plan view of a conventional grid electrode.

With respect to electrodes 400, 450, 460 exhibiting nonuniform contact distribution, the particular contacts 410a-c may be coupled to particular stimulation signals at a stimulation signal source. In contrast to neural simulation delivered through a conventional grid electrode 100 such as that shown in FIG. 1, stimulation delivered using an electrode exhibiting nonuniform contact separation or distribution may produce nonuniform stimulation field densities within or across predetermined stimulation regions. This may advantageously enhance neural stimulation efficacy by concentrating or reducing simulation in particular target areas.

In accordance with the present invention, one manner of providing an electrode having desired or intended neural stimulation characteristics involves the use of contacts of different peripheries or areas. The description hereafter details various multi-contact electrode embodiments having nonuniform contact periphery or area, possibly in conjunction with nonuniform contact separation. Relative to various embodiments described hereafter, like and/or analogous elements may be indicated with like reference numbers for ease of understanding.

Figure 5A:
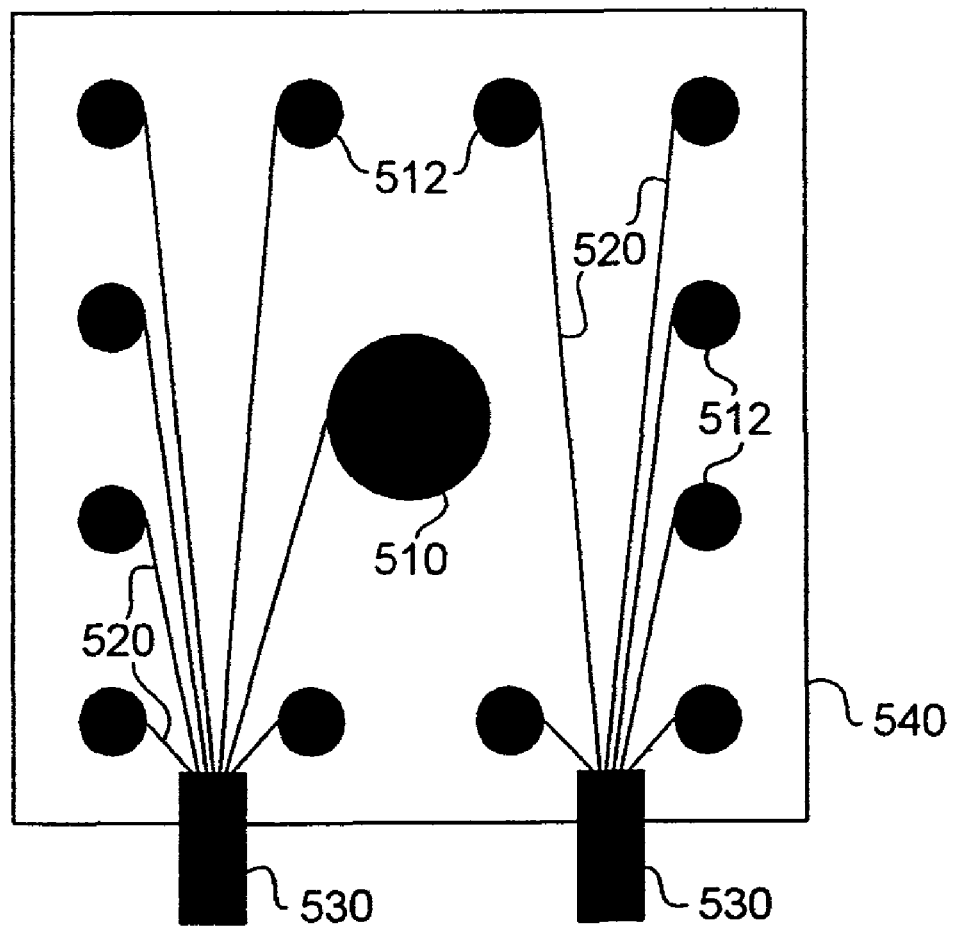
FIG. 5A is a plan view of an electrode exhibiting nonuniform contact sizes, areas, or peripheries according to an embodiment of the invention.

FIG. 5A is a plan view of an electrode 500 exhibiting variations in contact sizes, areas, and/or peripheries according to an embodiment of the invention. Such an electrode 500 may comprise at least one disk shaped contact 510 characterized by a first size, area, or circumference; one or more identically or essentially identically shaped contacts 512 characterized by a second size, area, or circumference; a lead wire 520 coupled to each contact 510, 512; a set of electrode leads 530 into which lead wires 520 may be organized and/or routed; and a medium, substrate, or backing upon and/or within which the contacts 510, 512, portions of the lead wires 520, and possibly portions of the electrode lead 530 may reside. The contacts 510, 512, lead wires 520, substrate 540, and one or more portions of the electrode leads 530 may be implemented using biocompatible materials in a manner identical and/or analogous to that described above.

A contact 510 characterized by the first size or area may be larger than a contact 512 characterized by the second size or area. In the embodiment shown in FIG. 5A, a larger-area disk shaped contact 510 is centrally positioned relative to a plurality of smaller-area disk shaped contacts 512 that are organized in accordance with a particular pattern. Depending upon embodiment details and/or neural stimulation requirements, electrodes constructed in accordance with the present invention may include various numbers of contacts characterized by the first size or area, the second size or area, other sizes or areas, and/or other contact shapes. Such contacts may be positioned, organized, or oriented with respect to each other and/or a substrate 540 in a wide variety of manners. Additional embodiments that employ a larger-area central contact 510 and a plurality of peripheral smaller-area contacts 512 are described in detail hereafter.

Figure 5B:
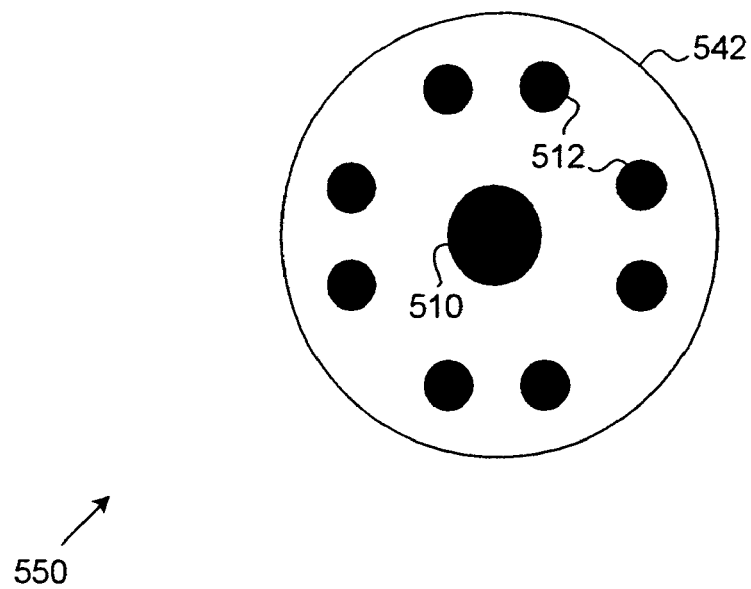
FIG. 5B is a plan view of a circular multi-contact electrode exhibiting nonuniform contact sizes or areas according to an embodiment of the invention.

FIG. 5B is a plan view of a circular multi-contact electrode 550 exhibiting nonuniform contact sizes according to an embodiment of the invention. In one embodiment, the circular multi-contact electrode 550 comprises a larger-area central contact 510; a plurality of smaller-area peripheral contacts 512 positioned relative to the central contact 510 in accordance with a predetermined pattern; and a substrate, medium, or backing 542 upon and/or within which the contacts 510, 512 may reside. To simplify understanding, individual lead wires and an electrode lead are not shown in FIG. 5B. Notwithstanding, each contact 510, 512 may be coupled to a corresponding lead wire, and lead wires may be organized and/or grouped into an electrode lead in a manner analogous to that shown in FIG. 5A. Each element of the circular multi-contact electrode 550 may be implemented using conventional biocompatible materials, in a manner previously indicated.

Figure 5C:
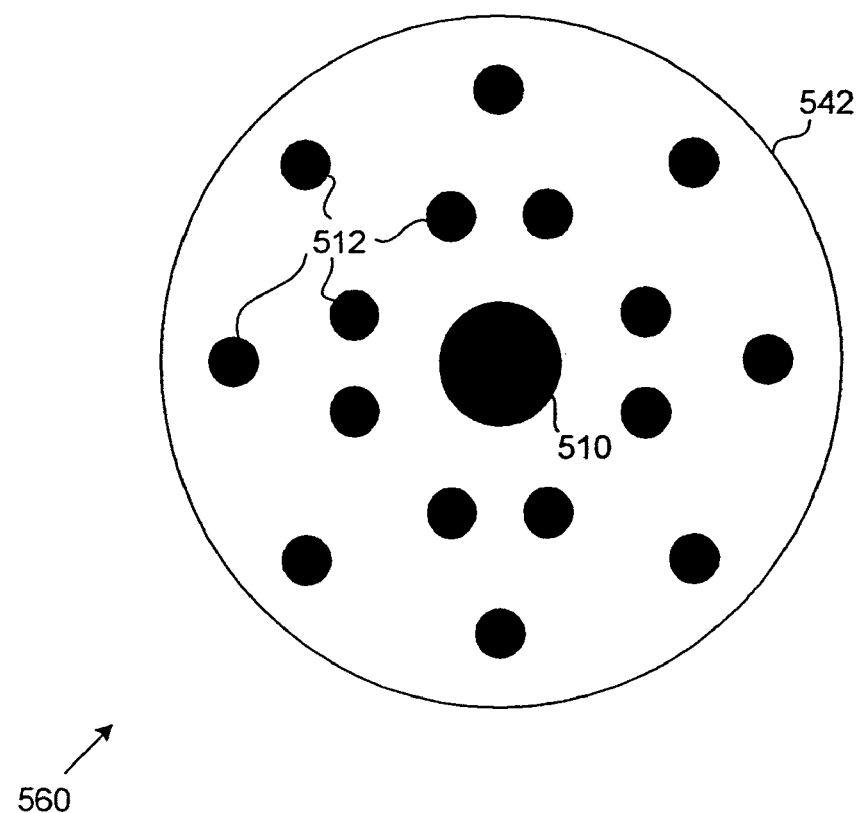
FIG. 5C is a plan view of a circular multi-contact electrode exhibiting nonuniform contact sizes or areas and nonuniform contact separation according to an embodiment of the invention.

FIG. 5C is a plan view of a circular multi-contact electrode 560 exhibiting nonuniform contact sizes and nonuniform contact separation according to an embodiment of the invention. The circular multi-contact electrode 560 of FIG. 5C may be structurally similar or analogous to the circular multi-contact electrode 460 of FIG. 4C, and may comprise a larger-area central contact 510 and a set of peripheral contacts 512 that reside upon and/or within a generally circular substrate or medium 542. The smaller-area peripheral contacts 512 may be organized or positioned in accordance with a set of predetermined patterns relative to the larger-area central contact 510. As in FIGS. 4C and 5B, individual lead wires and an electrode lead are not shown in FIG. 5C for ease of understanding. Nonetheless, each contact 510, 512 may be coupled to a corresponding lead wire, and lead wires may be organized and/or grouped into an electrode lead in a manner analogous to that shown in FIG. 5A. In addition, each element of the circular multi-contact electrode 560 may be implemented in a previously indicated manner using conventional biocompatible materials.

Relative to a smaller-area contact 512, a larger-area contact 510 exhibits a larger signal transfer area. A larger-area contact 510 may therefore facilitate more efficient delivery of larger magnitude stimulation signals than a smaller-area contact 512. An electrode characterized by nonuniform contact area may advantageously exhibit a lower effective impedance than, for example, a conventional grid electrode 100, and may provide enhanced efficiency neural stimulation.

Another manner of providing or approximating an intended electric or stimulation field distribution is through the selective use of electrode-based or on-electrode couplings, links, connections, and/or shunts between contacts. In the context of the present invention, an electrode-based or on-electrode contact coupling may comprise a contact-to-contact coupling and/or connection that originates at one contact and terminates at one or more other contacts. On-electrode contact couplings may include one or more portions that reside within, upon, above and/or beneath a substrate, and/or proximate to the substrate's spatial bounds. The description hereafter details various multi-contact electrode embodiments that may selectively exploit on-electrode contact couplings or interconnections, possibly in conjunction with nonuniform contact separation and/or nonuniform contact area. Relative to various embodiments described hereafter, like and/or analogous elements may be indicated with like reference numbers for ease of understanding.

Figure 6A:
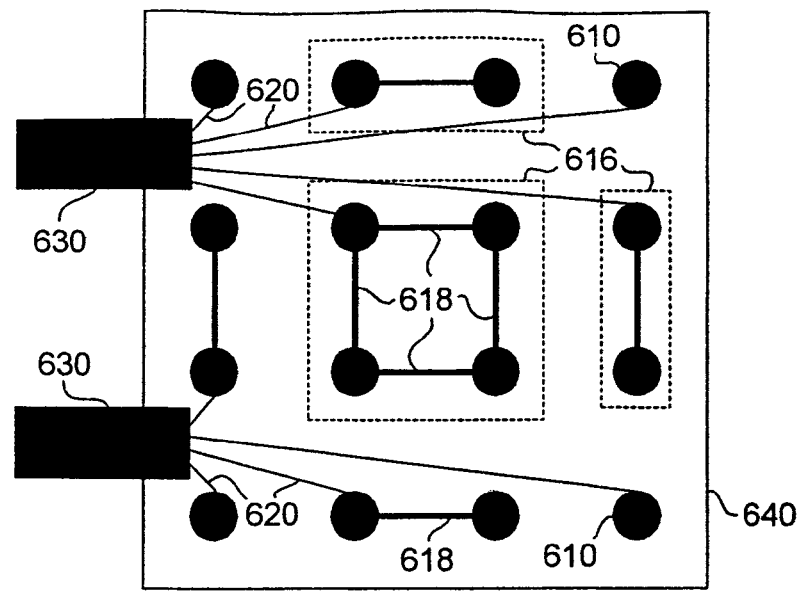
FIG. 6A is a plan view of an electrode having selectively interconnected contacts according to an embodiment of the invention.

FIG. 6A is a plan view of an electrode 600 having selectively coupled, connected, and/or interconnected contacts according to an embodiment of the invention. In one embodiment, the electrode 600 comprises a plurality of contacts 610; one or more electrically interdependent, isoelectric, and/or essentially isoelectric contact groups 616; lead wires 620 corresponding to each contact 610 and each isoelectric contact group 616; a set of electrode leads 630 into which lead wires 620 may be grouped or-organized; and a substrate or medium 640 upon and/or within which the contacts 610, the contact groups 616, portions of the lead wires 620, and possibly portions of the electrode leads 630 may reside. In one embodiment, the lead wires 620, the electrode lead 630, and the substrate 640 are formed from conventional biocompatible materials.

In one embodiment, an isoelectric contact group 616 comprises two or more contacts 610 having on-electrode couplings, links, connections, interconnections and/or shunts 618 therebetween. A contact interconnection 618 within an isoelectric contact group 616 may reside in a particular plane relative to contact, contact group, and/or electrode surfaces intended to impinge or impress upon a patient's neural tissue. Contacts 610 and/or contact groups 616 may be implemented using one or more biologically compatible, electrically conductive materials, such as Stainless Steel, Platinum, Platinum-Iridium, and/or other materials. Contact groups 616 and/or contact interconnections 618 may be formed using highly conductive materials, materials having variable and/or adjustable conductive properties, and/or materials exhibiting particular impedance characteristics.

An electrode 600 having contact couplings and/or interconnections 618 in accordance with the present invention may be manufactured in a variety of manners. For example, various types of preformed isoelectric contact groups 616 may be cut, stamped, formed, molded, or otherwise manufactured in a manner analogous to that for contacts 610. One or more portions of a preformed contact group 616 may exhibit bar, barbell, rectangular, or other types of shapes. Preformed contact groups 616 may be positioned upon or within a substrate 640 and coupled or connected to lead wires 620 in a manner essentially identical to that for contacts 610. As another manufacturing example, contacts 610, lead wires 620, and/or an electrode lead 630 may be formed, placed, and/or organized using conventional techniques, after which desired contact interconnections 618 may be formed or fabricated using selective masking and material deposition techniques, thereby forming isoelectric contact groups 616. As yet another example, contacts 610 organized in accordance with a given pattern and exhibiting selective contact interconnections 618 may be formed using flex circuit and/or membrane circuit fabrication techniques. One or more portions of a flex or membrane circuit may be encased, encapsulated, covered, or surrounded by Silicone, Silastic® (Dow Corning Corporation, Midland, Mich.), and/or other materials to ensure appropriate biocompatibility.

Figure 6B:
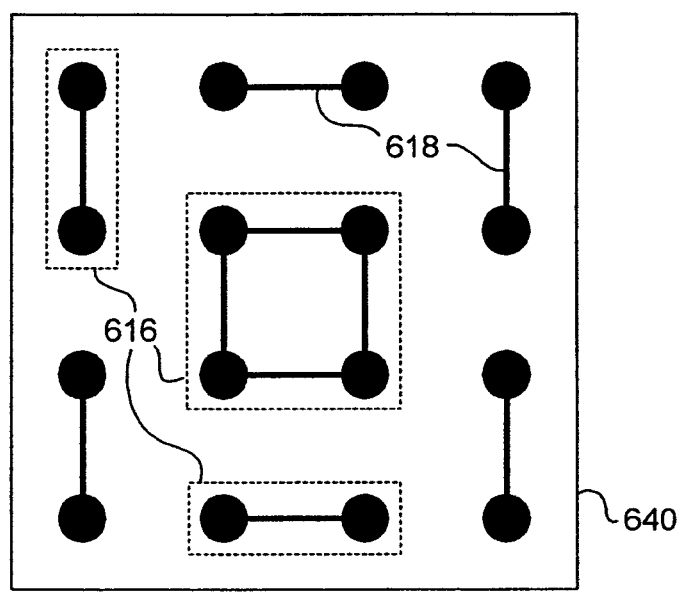
FIG. 6B is a plan view of an electrode having selectively interconnected contacts according to another embodiment of the invention.

FIG. 6B is a plan view of an electrode 650 having selective contact interconnections 618 according to another embodiment of the invention. The electrode 650 shown in FIG. 6B may be structurally identical or analogous to that shown in FIG. 6A, with the exception that it comprises a plurality of contact groups 616, and omits individual contacts 610 that are electrically independent. The contact interconnections 618 of FIG. 6B reside in different positions relative to those in FIG. 6A.

Figure 6C:
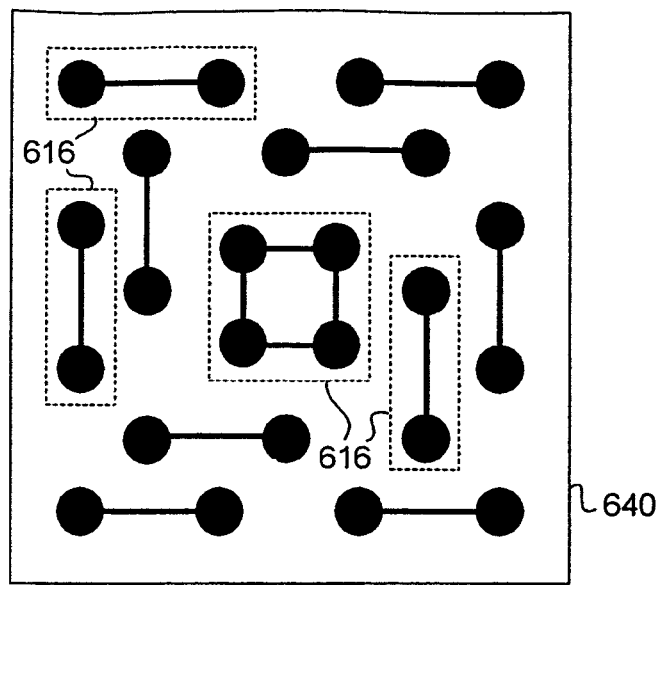
FIG. 6C is a plan view of an electrode having selectively interconnected contacts and nonuniform contact distribution according to an embodiment of the invention.

FIG. 6C is a plan view of an electrode 652 having selectively coupled and/or interconnected contacts and nonuniform contact separation or spacing according to an embodiment of the invention. The electrode 652 shown in FIG. 6C exhibits a structural and/or geometric correspondence to the electrode 400 shown in FIG. 4A. In one embodiment, the electrode 652 comprises a plurality of isoelectric contact groups 616 that reside upon a substrate or medium 640. For ease of understanding, lead wires and an electrode lead are not shown in FIG. 6C. Notwithstanding, any given contact group 616 may be coupled to a corresponding lead wire, and lead wires may be organized and/or grouped into an electrode lead in a manner identical or essentially identical to that previously described. Each element of the electrode 652 of FIG. 6C may be implemented using biocompatible materials in manners previously described.

Figure 6D:
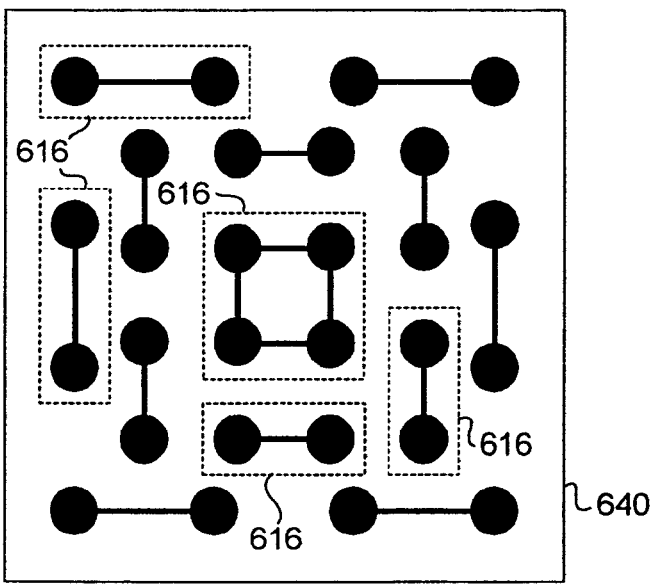
FIG. 6D is a plan view of an electrode having selectively interconnected contacts and nonuniform contact distribution according to another embodiment of the invention.

FIG. 6D is a plan view of an electrode 654 having selectively coupled and/or interconnected contacts and nonuniform contact separation according to another embodiment of the invention. The electrode 654 shown in FIG. 6D exhibits a structural correspondence to the electrode 450 shown in FIG. 4B. In one embodiment, the electrode 654 comprises a plurality of isoelectric contact groups 616 that reside upon a substrate or medium 640. Lead wires and an electrode lead are not shown in FIG. 6D to simplify understanding. Nonetheless, any given contact group 616 may be coupled to a corresponding lead wire, and lead wires may be organized and/or grouped into an electrode lead in a manner identical or essentially identical to that previously described. Each element of the electrode 654 of FIG. 6D may be implemented using biocompatible materials in manners previously described.

Figure 6E:
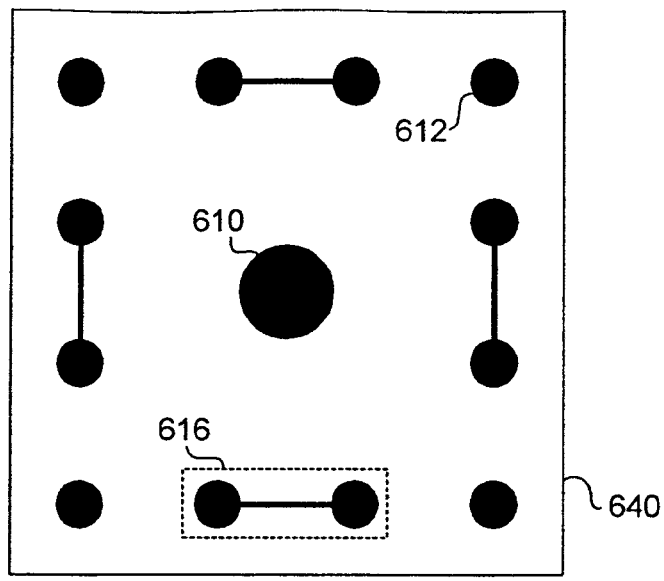
FIG. 6E is a plan view of an electrode having selectively interconnected contacts and nonuniform contact areas or peripheries according to an embodiment of the invention.

FIG. 6E is a plan view of an electrode 660 having selectively interconnected contacts and nonuniform contact areas according to an embodiment-of the invention. The electrode 660 shown in FIG. 6E exhibits a structural correspondence to the electrode 500 shown in FIG. 5A. In one embodiment, the electrode 660 comprises a substrate 640 upon and/or within which a larger-area central contact 610, a plurality of smaller-area peripheral contacts 612, and a plurality of isoelectric contact groups 616 may reside in accordance with a set of predetermined patterns. To simplify understanding, lead wires and an electrode lead are not shown in FIG. 6E. Nonetheless, the central contact 610, any given peripheral contact 612, and any given contact group 616 may each be coupled to a corresponding lead wire, and lead wires may be organized and/or grouped into an electrode lead in a manner identical or essentially identical to that previously described. Each element of the electrode 660 of FIG. 6E may be implemented using biocompatible materials in manners previously described.

Figure 6F:
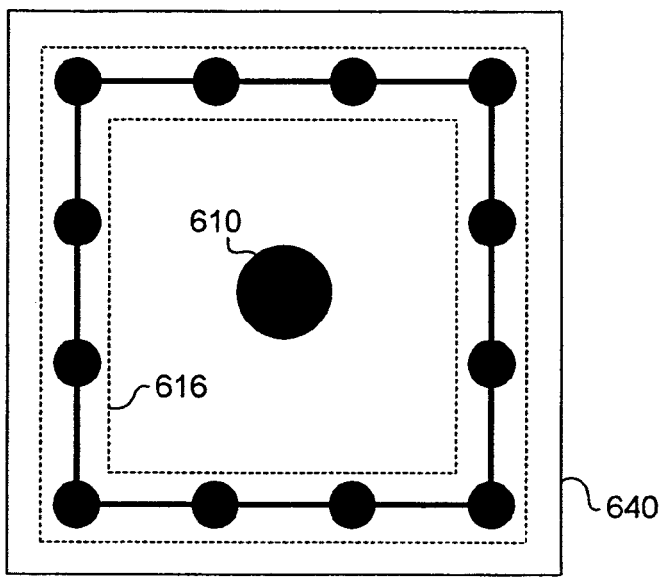
FIG. 6F is a plan view of an electrode having selectively interconnected contacts and nonuniform contact areas according to another embodiment of the invention.

FIG. 6F is a plan view of an electrode 662 having selectively interconnected contacts and nonuniform contact areas according to another embodiment of the invention. The electrode 662 shown in FIG. 6F exhibits a structural correspondence to the electrode 500 of FIG. 5A and the electrode 660 of FIG. 6E. The electrode 662 of FIG. 6F may comprise a substrate or medium 640 upon and/or within which a central contact 610 and a peripherally positioned isoelectric contact group 616 reside. In the embodiment shown, the isoelectric contact group 616 surrounds the central contact 610. Thus, the electrode 662 of FIG. 6F may provide a generally uniform stimulation field distribution capable of approximating that of an annular electrode 200. In FIG. 6F, lead wires and an electrode lead are not shown to simplify understanding. Nonetheless, the central contact 610 and the contact group 616 may each be coupled to a corresponding lead wire, and lead wires may be organized and/or grouped into an electrode lead in a manner identical or essentially identical to that described above. Each element of the electrode 662 of FIG. 6F may be implemented using biocompatible materials in manners previously described.

Figure 6G:
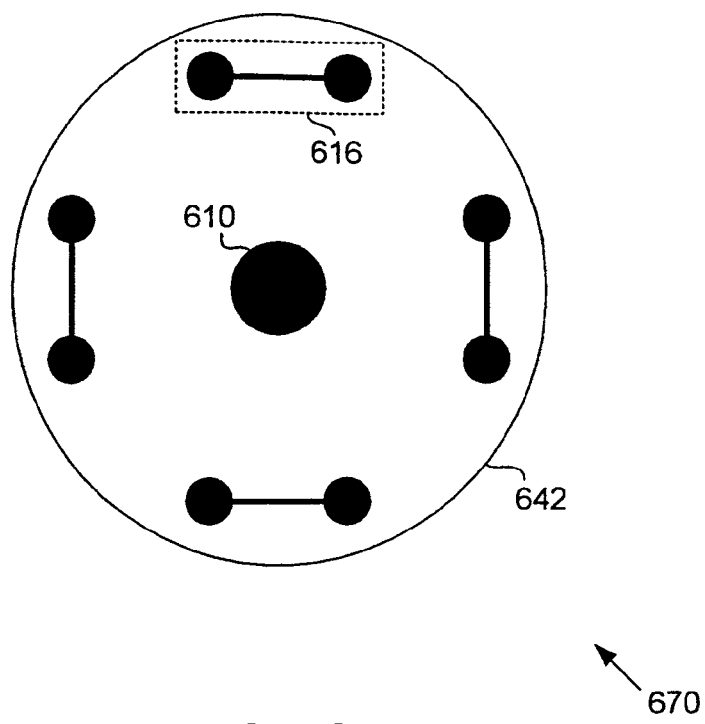
FIG. 6G is a plan view of a circular multi-contact electrode having selectively interconnected contacts and nonuniform contact areas according to an embodiment of the invention.

FIG. 6G is a plan view of a circular multi-contact electrode 670 having selectively interconnected contacts and nonuniform contact areas according to an embodiment of the invention. The electrode 670 of FIG. 6G exhibits a structural correspondence to the electrode 550 of FIG. 5B. The electrode 670 of FIG. 6G may comprise a larger-area central contact 610; a plurality of contact groups 616 peripherally positioned with respect thereto; and a generally circular substrate or medium 642 upon and/or within which the central contact 610 and the contact groups 616 may reside. Due to the positioning of the contact groups 616 relative to the central contact 610, the electrode 670 of FIG. 6G may provide a reasonably or generally uniform stimulation field distribution capable of approximating that of an annular electrode 200. To simplify understanding, lead wires and an electrode lead are not shown in FIG. 6G. Notwithstanding, the central contact 610 and any given contact group 616 may be coupled to corresponding lead wires, and lead wires may be organized and/or grouped into an electrode lead in a manner identical or essentially identical to that previously described. Each element of the electrode 670 of FIG. 6G may be implemented using biocompatible materials in manners previously described.

Figure 6H:
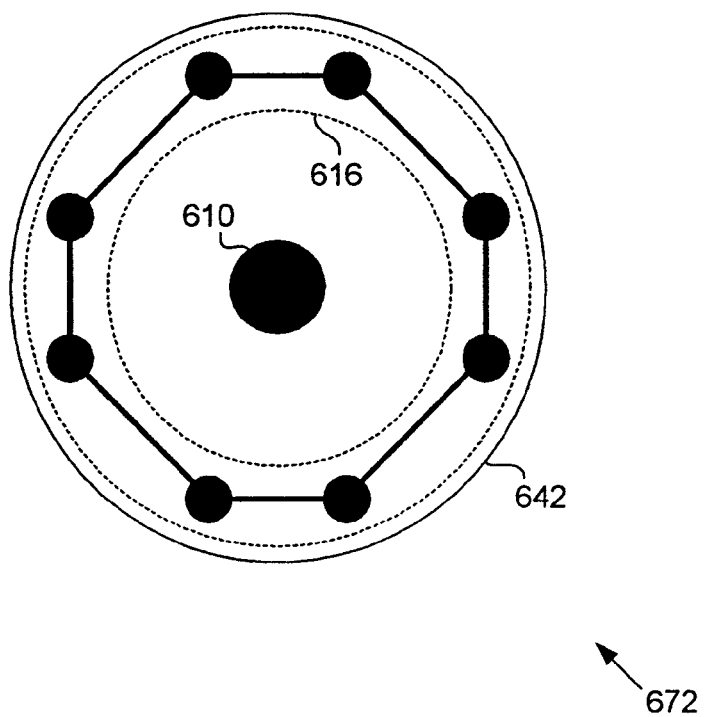
FIG. 6H is a plan view of a circular multi-contact electrode having selectively interconnected contacts and nonuniform contact areas according to another embodiment of the invention.

FIG. 6H is a plan view of a circular multi-contact electrode 672 having selectively interconnected contacts and nonuniform electrode area according to another embodiment of the invention. The electrode 672 of FIG. 6H exhibits a structural correspondence to the electrode 550 of FIG. 5B and the electrode 670 of FIG. 6G. The electrode 670 of FIG. 6H comprises a larger-area central contact 610 and a surrounding contact group 616, which may be mounted or positioned upon and/or within a generally circular substrate or backing 642. The electrode 672 of FIG. 6H may provide a generally or highly uniform stimulation field distribution capable of approximating that of an annular electrode 200 due to the geometric structure of its contact group 616 and the position or orientation of the contact group 616 relative to the central contact 610. To simplify understanding, lead wires and an electrode lead are not shown in FIG. 6H. Notwithstanding, the central contact 610 and the given contact group 616 may each be coupled to a corresponding lead wire, and lead wires may be organized and/or grouped into an electrode lead in a manner identical or essentially identical to that previously described. Each element of the electrode 672 of FIG. 6H may be implemented using biocompatible materials in manners previously described.

Figure 6I:
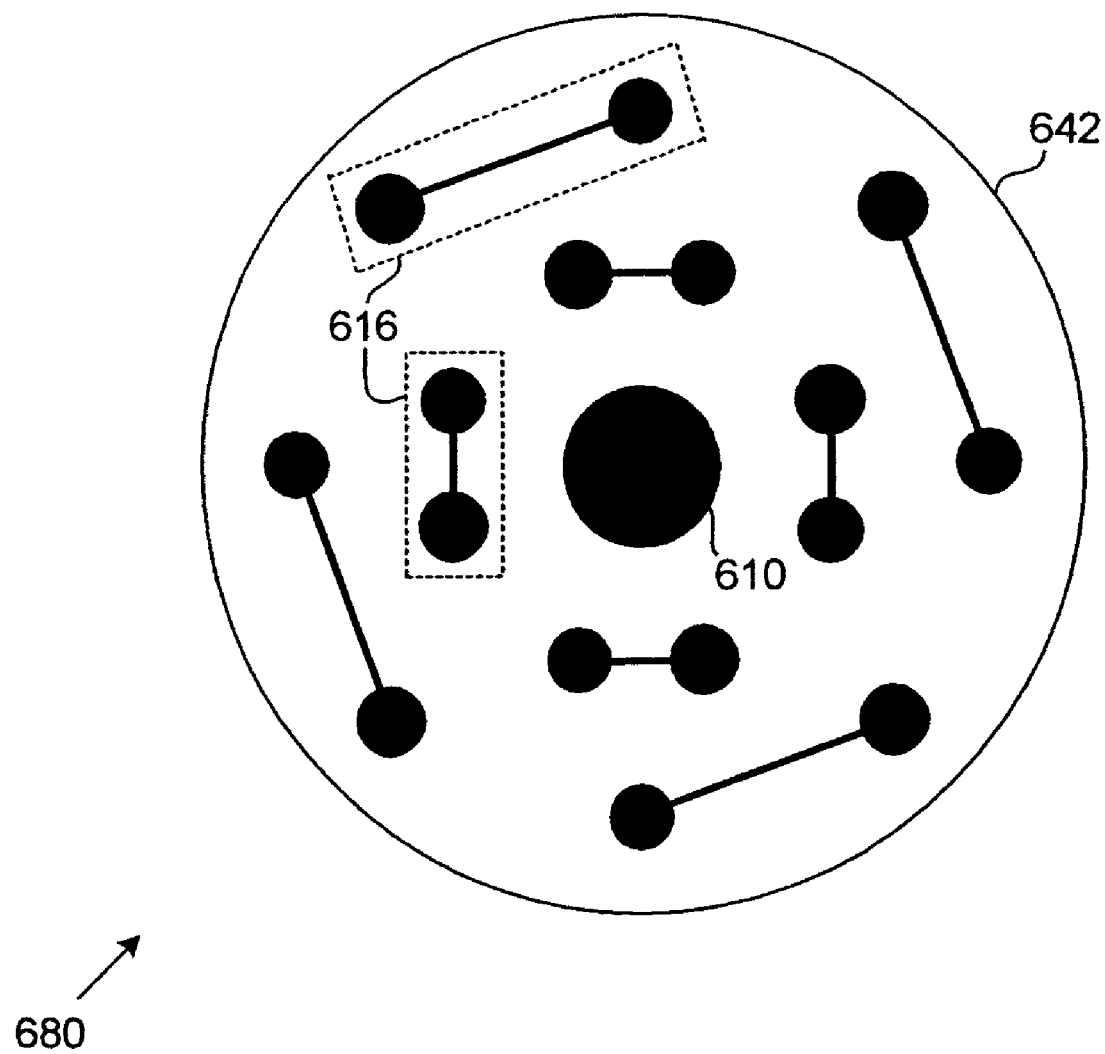
FIG. 6I is a plan view of a circular multi-contact electrode having selectively interconnected contacts, nonuniform contact areas, and nonuniform contact group distribution according to an embodiment of the invention.

FIG. 6I is a plan view of a circular multi-contact electrode 680 having selectively interconnected contacts, nonuniform contact areas, and nonuniform contact group separation according to an embodiment of the invention. The electrode 680 of FIG. 6I maintains a structural and/or geometric correspondence to the electrode 560 of FIG. 5C, and comprises a larger area central contact 610 and a plurality of contact groups 616 peripherally positioned relative thereto, where the central contact 610 and the contact groups 616 may be positioned or mounted upon and/or within a generally circular substrate or medium 642. To simplify understanding, lead wires and an electrode lead are not shown in FIG. 6H. Notwithstanding, the central contact 610 and any given contact group 616 may be coupled to a corresponding lead wire, and lead wires may be organized and/or grouped into an electrode lead in a manner identical or essentially identical to that previously described. Each element of the electrode 680 of FIG. 6I may be implemented using biocompatible materials in manners previously described.

An electrode having selectively positioned on-electrode contact groups 616, which may be formed from appropriate types of couplings or interconnections 618 between contacts 610, may produce a predetermined or preconfigured stimulation field distribution capable of providing an intended or desired type of neural stimulation. In addition, such an electrode may advantageously exhibit reduced complexity, and thus enhanced reliability, since any given isoelectric contact group 616 may be coupled to a single lead wire rather than coupling individual lead wires to each contact 610 within the contact group 616.

Electrodes may be designed in accordance with the present invention based upon stimulation signal characteristics and/or stimulation field distribution requirements associated with a given neural stimulation situation. Electrode embodiments described herein may be modified and/or generalized in a variety of manners. For example, an annular or arc electrode may include one or more on-electrode contact interconnections. As another example, one or more electrode embodiments described above may include fewer or additional contacts and/or contact groups. As yet another example, an electrode designed in accordance with the present invention may include one or more arc shaped, disk shaped, and/or otherwise shaped contacts, which may vary in spatial distribution and/or contact area or periphery. Such an electrode may further include on-electrode contact interconnections or couplings between identically, similarly, and/or differently shaped contacts. The present invention encompasses these and other variations, and is limited only by the following claims.

I claim:

1. An electrode suitable for neural stimulation comprising:
   a substrate configured to be implanted in a human body;
   a first set of electrical contacts carried by the substrate and organized in accordance with a first pattern; and
   a second set of electrical contacts carried by the substrate and organized in accordance with a second pattern,
   wherein a separation distance between a contact within the first set of electrical contacts and a contact within the second set of electrical contacts is unequal to the separation distance between contacts in first set electrical contacts and is unequal to the separation distance between contacts in the second set of electrical contacts and further wherein at least one contact within the second set of electrical contacts is disk shaped.

2. The electrode of claim 1, wherein each contact within the second set of electrical contacts is disk shaped.

3. An electrode suitable for neural stimulation comprising:
   a substrate configured to be implanted in a human body;
   a centrally positioned electrical contact carried by the substrate and having a first area; and
   a plurality of peripherally positioned electrical contacts carried by the substrate, at least one peripherally positioned electrical contact having an essentially identical shape as the centrally positioned contact and a second area different than the first area.

4. The electrode of claim 3, wherein each peripherally positioned electrical contact has an essentially identical shape as the centrally positioned contact.

5. An electrode suitable for neural stimulation comprising:
   a substrate configured to be implanted in a human body; and
   a plurality of electrical contacts carried by the substrate and spatially distributed in a nonuniform manner, the plurality of electrical contacts including at least two contacts having different peripheries, wherein the plurality of electrical contacts includes at least two contacts having an on-electrode coupling therebetween.

6. An electrode suitable for neural stimulation comprising:
   a substrate configured to be implanted in a human body; and
   a plurality of electrical contacts carried by the substrate and spatially distributed in a nonuniform manner; and
   an on-electrode coupling between at least two contacts within the plurality of electrical contacts.

7. The electrode of claim 6, wherein at least two contacts within the plurality of electrical contacts have different peripheries.

* * * * *